(12) United States Patent
Hooven

(10) Patent No.: US 7,288,092 B2
(45) Date of Patent: Oct. 30, 2007

(54) METHOD AND APPARATUS FOR ABLATING CARDIAC TISSUE WITH GUIDE FACILITY

(75) Inventor: Michael D. Hooven, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 0 days.

(21) Appl. No.: 10/829,701

(22) Filed: Apr. 22, 2004

(65) Prior Publication Data

US 2004/0249368 A1    Dec. 9, 2004

Related U.S. Application Data

(60) Provisional application No. 60/547,364, filed on Feb. 24, 2004, provisional application No. 60/464,713, filed on Apr. 23, 2003.

(51) Int. Cl.
*A61B 18/14* (2006.01)
*A61B 18/18* (2006.01)

(52) U.S. Cl. ............................ 606/51; 128/898; 606/32

(58) Field of Classification Search .................. 606/41, 606/205–211, 32–52; 128/898
See application file for complete search history.

(56) References Cited

U.S. PATENT DOCUMENTS

| | | | |
|---|---|---|---|
| 1,127,948 A | 2/1915 | Wappler | |
| 2,004,559 A | 6/1935 | Wappler et al. | |
| 3,470,875 A | 10/1969 | Johnson et al. | |
| 3,630,207 A | 12/1971 | Kahn et al. | 128/350 |
| 3,901,242 A | 8/1975 | Storz | 128/303 |
| 4,043,342 A | 8/1977 | Morrison, Jr. | 128/303 |
| 4,312,337 A | 1/1982 | Donohue et al. | |
| 4,353,371 A | 10/1982 | Cosman | 128/303 |
| 4,492,231 A | 1/1985 | Auth | 128/303 |

(Continued)

FOREIGN PATENT DOCUMENTS

DE            43 13 903 C1        9/1994

(Continued)

OTHER PUBLICATIONS

English abstract re Japanese Patent Application No. JP 1996000275351, published Apr. 28, 1997.

(Continued)

*Primary Examiner*—Henry M Johnson, III
(74) *Attorney, Agent, or Firm*—Cook, Alex, McFarron, Manzo, Cummings & Mehler, Ltd.

(57) ABSTRACT

A method and apparatus for ablation of cardiac tissue at a selected cardiac location is achieved by providing at least one flexible elongated guide facility having a first end, a second end, and an intermediate portion extending between the first and second ends and by providing an ablation instrument which includes at least a pair of relatively moveable clamping jaws being disposed to engage and ablate the selected cardiac location. Each guide facility is adapted for introduction into a patient's chest through an opening and for advancement to the selected cardiac location such that the intermediate portion engages the selected cardiac location and the guide facility is withdrawn through the instrument receiving passage. At least one jaw of the ablation instrument engages with the guide facility and is guided to the selected cardiac location with the aid of the guide facility to ablate the selected cardiac location.

13 Claims, 12 Drawing Sheets

U.S. PATENT DOCUMENTS

| | | | |
|---|---|---|---|
| 4,590,934 A | 5/1986 | Malis et al. ............... 128/303 |
| 4,706,667 A | 11/1987 | Roos ........................ 128/303 |
| 4,732,149 A | 3/1988 | Sutter ....................... 128/303 |
| 4,802,475 A | 2/1989 | Weshahy .................. 128/303 |
| 4,940,064 A | 7/1990 | Desai ........................ 128/784 |
| 5,009,661 A | 4/1991 | Michelson |
| 5,013,312 A | 5/1991 | Parins et al. ................. 606/37 |
| 5,033,477 A | 7/1991 | Chin et al. |
| 5,044,947 A | 9/1991 | Sachdeva et al. |
| 5,071,428 A | 12/1991 | Chin et al. |
| 5,083,565 A | 1/1992 | Parins ....................... 128/642 |
| 5,085,657 A | 2/1992 | Ben-Simhon ............... 606/42 |
| 5,087,243 A | 2/1992 | Avitall ....................... 604/20 |
| 5,116,332 A | 5/1992 | Lottick ...................... 606/42 |
| 5,125,928 A | 6/1992 | Parins et al. |
| 5,147,355 A | 9/1992 | Friedman ................... 606/23 |
| 5,190,541 A | 3/1993 | Abele et al. ................. 606/46 |
| 5,207,691 A | 5/1993 | Nardella .................... 606/142 |
| 5,217,460 A | 6/1993 | Knopfler .................... 606/52 |
| 5,231,995 A | 8/1993 | Desai ........................ 128/784 |
| 5,242,441 A | 9/1993 | Avitall ....................... 606/41 |
| 5,242,458 A | 9/1993 | Bendel et al. |
| 5,250,047 A | 10/1993 | Rydell ....................... 606/48 |
| 5,250,075 A | 10/1993 | Badie ........................ 606/207 |
| 5,263,493 A | 11/1993 | Avitall ...................... 607/122 |
| 5,269,326 A | 12/1993 | Verrier ...................... 128/642 |
| 5,269,780 A | 12/1993 | Roos ......................... 606/42 |
| 5,281,215 A | 1/1994 | Milder ....................... 606/20 |
| 5,281,216 A | 1/1994 | Klicek ....................... 606/42 |
| 5,293,869 A | 3/1994 | Edwards et al. ............ 128/642 |
| 5,306,234 A | 4/1994 | Johnson |
| 5,318,589 A | 6/1994 | Lichtman ................... 606/205 |
| 5,323,781 A | 6/1994 | Ideker et al. |
| 5,327,905 A | 7/1994 | Avitall ....................... 128/772 |
| 5,354,297 A | 10/1994 | Avitall ....................... 606/45 |
| 5,357,956 A | 10/1994 | Nardella .................... 128/642 |
| 5,397,339 A | 3/1995 | Desai ........................ 607/116 |
| 5,403,312 A | 4/1995 | Yates et al. ................. 606/50 |
| 5,423,807 A | 6/1995 | Milder ....................... 606/20 |
| 5,429,131 A | 7/1995 | Scheinman et al. ......... 128/642 |
| 5,429,636 A | 7/1995 | Shikhman et al. .......... 606/41 |
| 5,438,302 A | 8/1995 | Goble ....................... 331/167 |
| 5,441,483 A | 8/1995 | Avitall ....................... 604/95 |
| 5,443,463 A | 8/1995 | Stern et al. ................. 606/51 |
| 5,445,638 A | 8/1995 | Rydell et al. ................ 606/51 |
| 5,449,355 A | 9/1995 | Rhum et al. ................ 606/41 |
| 5,451,223 A | 9/1995 | Ben-Simhon ............... 606/42 |
| 5,452,733 A | 9/1995 | Sterman et al. |
| 5,454,370 A | 10/1995 | Avitall ....................... 128/642 |
| 5,465,716 A | 11/1995 | Avitall ....................... 128/642 |
| 5,472,441 A | 12/1995 | Edwards et al. ............. 606/41 |
| 5,478,309 A | 12/1995 | Sweezer et al. .............. 604/4 |
| 5,480,409 A | 1/1996 | Riza .......................... 606/205 |
| 5,487,385 A | 1/1996 | Avitall ....................... 128/642 |
| 5,496,312 A | 3/1996 | Klicek ....................... 606/34 |
| 5,500,011 A | 3/1996 | Desai ........................ 607/116 |
| 5,500,012 A | 3/1996 | Brucker et al. |
| 5,531,744 A | 7/1996 | Nardella et al. ............. 606/48 |
| 5,536,267 A | 7/1996 | Edwards et al. ............. 606/41 |
| 5,549,636 A | 8/1996 | Li |
| 5,555,883 A | 9/1996 | Avitall ....................... 128/642 |
| 5,562,699 A | 10/1996 | Heimberger et al. |
| 5,562,700 A | 10/1996 | Huitema et al. |
| 5,562,721 A | 10/1996 | Marchlinski et al. ........ 607/99 |
| 5,564,440 A | 10/1996 | Swartz et al. ............... 128/898 |
| 5,571,215 A | 11/1996 | Sterman et al. |
| 5,575,766 A | 11/1996 | Swartz et al. |
| 5,575,805 A | 11/1996 | Li |
| 5,582,609 A | 12/1996 | Swanson et al. ............. 606/39 |
| 5,587,723 A | 12/1996 | Otake et al. ................. 345/118 |
| 5,595,183 A | 1/1997 | Swanson et al. ............ 128/697 |
| 5,599,350 A | 2/1997 | Schulze et al. .............. 606/51 |
| 5,611,813 A | 3/1997 | Lichtman ................... 606/205 |
| 5,620,459 A | 4/1997 | Lichtman ................... 606/205 |
| 5,642,736 A | 7/1997 | Avitall ....................... 128/772 |
| 5,655,219 A | 8/1997 | Jusa et al. ................... 370/338 |
| 5,672,174 A | 9/1997 | Gough et al. ................. 606/41 |
| 5,674,220 A | 10/1997 | Fox et al. .................... 606/51 |
| 5,680,860 A | 10/1997 | Imran |
| 5,683,384 A | 11/1997 | Gough et al. ................. 606/41 |
| 5,687,737 A | 11/1997 | Branham et al. ........... 128/710 |
| 5,688,270 A | 11/1997 | Yates et al. .................. 606/51 |
| 5,690,611 A | 11/1997 | Swartz et al. ................ 604/53 |
| 5,693,051 A | 12/1997 | Schulze et al. .............. 606/51 |
| 5,697,925 A | 12/1997 | Taylor ........................ 606/34 |
| 5,697,928 A | 12/1997 | Walcott et al. ............... 606/41 |
| 5,702,359 A | 12/1997 | Hofmann et al. ............. 604/20 |
| 5,702,390 A | 12/1997 | Austin et al. ................ 606/48 |
| 5,702,438 A | 12/1997 | Avitall ...................... 607/122 |
| 5,709,680 A | 1/1998 | Yates et al. .................. 606/50 |
| 5,718,703 A | 2/1998 | Chin .......................... 606/49 |
| 5,722,403 A | 3/1998 | McGee et al. .............. 128/642 |
| 5,725,512 A | 3/1998 | Swartz et al. ............... 604/280 |
| 5,728,143 A | 3/1998 | Gough et al. ............... 607/101 |
| 5,730,127 A | 3/1998 | Avitall ....................... 128/642 |
| 5,730,704 A | 3/1998 | Avitall ....................... 600/374 |
| 5,733,280 A | 3/1998 | Avitall ....................... 606/23 |
| 5,735,847 A | 4/1998 | Gough et al. ................. 606/45 |
| 5,735,849 A | 4/1998 | Baden et al. ................. 606/51 |
| 5,740,808 A | 4/1998 | Panescu et al. ............. 128/662 |
| 5,755,664 A | 5/1998 | Rubenstein ................ 600/377 |
| 5,755,717 A | 5/1998 | Yates et al. .................. 606/51 |
| 5,759,158 A | 6/1998 | Swanson .................... 600/508 |
| 5,776,130 A | 7/1998 | Buysse et al. |
| 5,782,827 A | 7/1998 | Gough et al. ................. 606/41 |
| 5,782,828 A | 7/1998 | Chen et al. .................. 606/42 |
| 5,785,706 A | 7/1998 | Bednarek .................... 606/41 |
| H1745 H | 8/1998 | Paraschac .................... 606/51 |
| 5,797,906 A | 8/1998 | Rhum et al. ................. 606/48 |
| 5,797,960 A | 8/1998 | Stevens et al. ............. 606/213 |
| 5,800,484 A | 9/1998 | Gough et al. ............... 607/104 |
| 5,807,393 A | 9/1998 | Williamson, IV et al. .... 606/32 |
| 5,807,395 A | 9/1998 | Mulier et al. ................ 606/41 |
| 5,810,804 A | 9/1998 | Gough et al. ................. 606/41 |
| 5,810,805 A | 9/1998 | Sutcu et al. ................. 606/45 |
| 5,810,811 A | 9/1998 | Yates et al. .................. 606/50 |
| 5,814,028 A | 9/1998 | Swartz et al. |
| 5,817,091 A | 10/1998 | Nardella et al. ............. 606/38 |
| 5,823,955 A | 10/1998 | Kuck et al. ................. 600/374 |
| 5,823,956 A | 10/1998 | Roth et al. .................. 600/374 |
| 5,829,447 A | 11/1998 | Stevens et al. ............. 128/898 |
| 5,833,690 A | 11/1998 | Yates et al. .................. 606/52 |
| 5,833,703 A | 11/1998 | Manushakian .............. 606/174 |
| 5,842,984 A | 12/1998 | Avitall ....................... 600/374 |
| 5,843,075 A | 12/1998 | Taylor ........................ 606/34 |
| 5,843,122 A | 12/1998 | Riza .......................... 606/207 |
| 5,846,238 A | 12/1998 | Jackson et al. .............. 606/41 |
| 5,849,011 A | 12/1998 | Jones et al. ................. 606/47 |
| 5,849,020 A | 12/1998 | Long et al. ................. 606/167 |
| 5,853,411 A | 12/1998 | Whayne et al. .............. 606/41 |
| 5,855,590 A | 1/1999 | Malecki et al. |
| 5,855,614 A | 1/1999 | Stevens et al. .............. 623/11 |
| 5,860,975 A | 1/1999 | Goble et al. ................. 606/45 |
| 5,863,290 A | 1/1999 | Gough et al. ................. 606/41 |
| 5,863,291 A | 1/1999 | Schaer ....................... 606/41 |
| 5,868,737 A | 2/1999 | Taylor et al. ................ 606/24 |
| 5,871,483 A | 2/1999 | Jackson et al. .............. 606/41 |
| 5,873,896 A | 2/1999 | Ideker ........................ 607/14 |
| 5,876,398 A | 3/1999 | Mulier et al. |
| 5,876,400 A | 3/1999 | Songer ....................... 606/45 |
| 5,876,401 A | 3/1999 | Schulze et al. .............. 606/51 |
| 5,891,135 A | 4/1999 | Jackson et al. .............. 606/41 |
| 5,891,136 A | 4/1999 | McGee et al. ............... 606/41 |
| 5,891,138 A | 4/1999 | Tu et al. |

| Patent # | Date | Inventor | Class |
|---|---|---|---|
| 5,893,863 A | 4/1999 | Yoon | 606/170 |
| 5,897,554 A | 4/1999 | Chia et al. | |
| 5,899,898 A | 5/1999 | Arless et al. | 606/22 |
| 5,899,899 A | 5/1999 | Arless et al. | 606/22 |
| 5,902,289 A | 5/1999 | Swartz et al. | 604/281 |
| 5,910,129 A | 6/1999 | Koblish et al. | 604/95 |
| 5,913,855 A | 6/1999 | Gough et al. | 606/41 |
| 5,921,924 A | 7/1999 | Avitall | 600/374 |
| 5,924,424 A | 7/1999 | Stevens et al. | 128/898 |
| 5,925,038 A | 7/1999 | Panescu et al. | 606/41 |
| 5,925,042 A | 7/1999 | Gough et al. | 606/41 |
| 5,928,229 A | 7/1999 | Gough et al. | 606/41 |
| 5,931,836 A | 8/1999 | Hatta et al. | 606/38 |
| 5,935,126 A | 8/1999 | Riza | 606/51 |
| 5,938,660 A | 8/1999 | Swartz et al. | 606/45 |
| 5,941,251 A | 8/1999 | Panescu et al. | 128/899 |
| 5,941,845 A | 8/1999 | Tu et al. | 604/53 |
| 5,944,718 A | 8/1999 | Austin et al. | 606/48 |
| 5,947,938 A | 9/1999 | Swartz et al. | 604/280 |
| 5,951,547 A | 9/1999 | Gough et al. | 606/41 |
| 5,951,552 A | 9/1999 | Long et al. | 606/46 |
| 5,954,665 A | 9/1999 | Ben-Haim | 600/515 |
| 5,961,514 A | 10/1999 | Long et al. | 606/41 |
| 5,967,976 A | 10/1999 | Larsen | 600/374 |
| 5,971,983 A | 10/1999 | Lesh | 606/41 |
| 5,972,026 A | 10/1999 | Laufer et al. | 607/96 |
| 5,980,516 A | 11/1999 | Mulier et al. | 606/41 |
| 5,980,517 A | 11/1999 | Gough | 606/41 |
| 5,984,281 A | 11/1999 | Hacker et al. | 261/71 |
| 5,997,533 A | 12/1999 | Kuhns | 606/41 |
| 6,010,516 A | 1/2000 | Hulka | 606/148 |
| 6,010,531 A | 1/2000 | Donlon et al. | 623/2 |
| 6,012,457 A | 1/2000 | Lesh | 128/898 |
| 6,013,074 A | 1/2000 | Taylor | 606/34 |
| 6,016,809 A | 1/2000 | Mulier et al. | 128/898 |
| 6,017,358 A | 1/2000 | Yoon et al. | 606/205 |
| 6,023,638 A | 2/2000 | Swanson | 600/510 |
| 6,024,740 A | 2/2000 | Lesh et al. | 606/34 |
| 6,024,741 A | 2/2000 | Williamson, IV et al. | 606/40 |
| 6,030,403 A | 2/2000 | Long et al. | 606/185 |
| 6,033,402 A | 3/2000 | Tu et al. | |
| 6,036,670 A | 3/2000 | Wijeratne et al. | 604/96 |
| 6,039,731 A | 3/2000 | Taylor et al. | 606/34 |
| 6,039,733 A | 3/2000 | Buyssee et al. | 606/40 |
| 6,039,748 A | 3/2000 | Savage et al. | 606/180 |
| 6,047,218 A | 4/2000 | Whayne et al. | 607/122 |
| 6,048,329 A | 4/2000 | Thompson et al. | 604/95 |
| 6,050,996 A | 4/2000 | Schmaltz et al. | |
| 6,064,902 A | 5/2000 | Haissaguerre et al. | |
| 6,068,653 A | 5/2000 | LaFontaine | |
| 6,071,281 A | 6/2000 | Burnside et al. | |
| 6,083,150 A | 7/2000 | Aznoian et al. | |
| 6,083,222 A * | 7/2000 | Klein et al. | 606/41 |
| 6,096,037 A | 8/2000 | Mulier et al. | |
| 6,110,098 A | 8/2000 | Renirie et al. | 600/16 |
| 6,113,595 A | 9/2000 | Muntermann | |
| 6,113,598 A | 9/2000 | Baker | |
| 6,117,101 A | 9/2000 | Diederich et al. | |
| 6,123,703 A | 9/2000 | Tu et al. | |
| 6,126,658 A | 10/2000 | Baker | |
| 6,142,994 A | 11/2000 | Swanson et al. | |
| 6,156,033 A | 12/2000 | Tu et al. | |
| 6,161,543 A | 12/2000 | Cox et al. | |
| 6,162,220 A | 12/2000 | Nezhat | |
| 6,193,713 B1 | 2/2001 | Geistert et al. | |
| 6,237,605 B1 | 5/2001 | Vaska et al. | |
| 6,264,087 B1 | 7/2001 | Whitman | |
| 6,267,761 B1 | 7/2001 | Ryan | |
| 6,273,887 B1 | 8/2001 | Yamauchi et al. | |
| 6,277,117 B1 | 8/2001 | Tetzlaff et al. | |
| 6,292,678 B1 | 9/2001 | Hall et al. | |
| 6,296,640 B1 | 10/2001 | Wampler et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,332,089 B1 | 12/2001 | Acker et al. | |
| 6,334,860 B1 | 1/2002 | Dorn | |
| 6,356,790 B1 | 3/2002 | Maguire et al. | |
| 6,358,249 B1 | 3/2002 | Chen et al. | |
| 6,391,024 B1 | 5/2002 | Sun et al. | |
| 6,443,970 B1 | 9/2002 | Schulze et al. | |
| 6,447,507 B1 | 9/2002 | Bednarek et al. | |
| 6,464,700 B1 | 10/2002 | Koblish et al. | |
| 6,474,340 B1 | 11/2002 | Vaska et al. | |
| 6,488,678 B2 | 12/2002 | Sherman | |
| 6,488,680 B1 | 12/2002 | Francischelli et al. | |
| 6,506,189 B1 | 1/2003 | Rittman, III et al. | |
| 6,517,536 B2 | 2/2003 | Hooven et al. | |
| 6,540,740 B2 | 4/2003 | Lehmann et al. | |
| 6,546,935 B2 | 4/2003 | Hooven | |
| 6,575,969 B1 | 6/2003 | Rittman, III et al. | |
| 6,610,055 B1 | 8/2003 | Swanson et al. | |
| 6,632,222 B1 | 10/2003 | Edwards et al. | |
| 6,679,882 B1 | 1/2004 | Kornerup | |
| 6,692,491 B1 | 2/2004 | Phan | |
| 2001/0031961 A1 | 10/2001 | Hooven | |
| 2001/0039419 A1 | 11/2001 | Francischelli et al. | |
| 2002/0002329 A1 | 1/2002 | Avitall | |
| 2002/0019629 A1 | 2/2002 | Dietz et al. | |
| 2002/0032440 A1 | 3/2002 | Hooven | |
| 2002/0052602 A1 | 5/2002 | Wang et al. | |
| 2002/0082595 A1 | 6/2002 | Langberg et al. | |
| 2002/0091382 A1 | 7/2002 | Hooven | |
| 2002/0091383 A1 | 7/2002 | Hooven | |
| 2002/0091384 A1 | 7/2002 | Hooven | |
| 2002/0099364 A1 | 7/2002 | Lalonde | |
| 2002/0103484 A1 | 8/2002 | Hooven | |
| 2002/0107513 A1 | 8/2002 | Hooven | |
| 2002/0107514 A1 | 8/2002 | Hooven | |
| 2002/0115990 A1 | 8/2002 | Acker | |
| 2002/0115993 A1 | 8/2002 | Hooven | |
| 2002/0120263 A1 | 8/2002 | Brown et al. | |
| 2002/0120316 A1 | 8/2002 | Hooven | |
| 2002/0128643 A1 | 9/2002 | Simpson et al. | |
| 2002/0183738 A1 | 12/2002 | Chee et al. | |
| 2003/0004507 A1 | 1/2003 | Francischelli et al. | |
| 2003/0009094 A1 | 1/2003 | Segner et al. | |
| 2003/0018329 A1 | 1/2003 | Hooven | |
| 2003/0028187 A1 | 2/2003 | Vaska et al. | |
| 2003/0032952 A1 | 2/2003 | Hooven | |
| 2003/0045871 A1 | 3/2003 | Jain et al. | |
| 2003/0050557 A1 | 3/2003 | Susil et al. | |
| 2003/0060822 A1 | 3/2003 | Schaer et al. | |
| 2003/0069572 A1 | 4/2003 | Wellman et al. | |
| 2003/0069577 A1 | 4/2003 | Vaska et al. | |
| 2003/0073991 A1 | 4/2003 | Francischelli et al. | |
| 2003/0078570 A1 | 4/2003 | Heiner et al. | |
| 2003/0078574 A1 | 4/2003 | Hall et al. | |
| 2003/0093104 A1 | 5/2003 | Bonner et al. | |
| 2003/0097124 A1 | 5/2003 | Lehmann et al. | |
| 2003/0100895 A1 | 5/2003 | Simpson et al. | |
| 2003/0114844 A1 | 6/2003 | Ormsby et al. | |
| 2003/0120268 A1 | 6/2003 | Bertolero et al. | |
| 2003/0125726 A1 | 7/2003 | Maguire et al. | |
| 2003/0125729 A1 | 7/2003 | Hooven | |
| 2003/0125730 A1 | 7/2003 | Berube et al. | |
| 2003/0130598 A1 | 7/2003 | Manning et al. | |
| 2003/0135207 A1 | 7/2003 | Langberg et al. | |
| 2003/0144657 A1 | 7/2003 | Bowe et al. | |
| 2003/0158548 A1 | 8/2003 | Phan et al. | |
| 2003/0171745 A1 | 9/2003 | Francischelli et al. | |
| 2003/0178032 A1 | 9/2003 | Ingle et al. | |

| | | |
|---|---|---|
| 2004/0216748 A1 * | 11/2004 | Chin .................. 128/898 |

FOREIGN PATENT DOCUMENTS

| | | |
|---|---|---|
| EP | 0 450 608 A1 | 10/1991 |
| EP | 0 765 639 | 4/1997 |
| WO | WO 92/05828 A1 | 4/1992 |
| WO | WO 93/25267 A1 | 12/1993 |
| WO | WO 97/10764 A1 | 3/1997 |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/04696 | 2/1999 |
| WO | WO 99/12487 | 3/1999 |
| WO | WO 99/44519 | 9/1999 |
| WO | WO 99/56486 | 11/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/27310 A2 | 5/2000 |
| WO | WO 00/27310 A3 | 5/2000 |
| WO | WO 00/27311 | 5/2000 |
| WO | WO 00/27312 | 5/2000 |
| WO | WO 00/27313 | 5/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 A1 | 11/2001 |
| WO | WO 01/82813 A2 | 11/2001 |
| WO | WO 01/82813 A3 | 11/2001 |
| WO | WO 02/087454 A1 | 11/2001 |

OTHER PUBLICATIONS

Yoshio Kosakai, M.D., et al., "Cox Maze Procedure for Chronic Atrial Fibrillation Associated with Mitral Valve Disease," The Journal of Thoracic and Cardiovascular Surgery, 1994; vol. 108, No. 6, pp. 1049-1055.

Ki-Bong, Kim, M.D., et al., Abstract "The Cox-Maze III Procedure for Atrial Fibrillation Associated with Rheumatic Mitral Valve Disease," The Annals of Thoracic Surgery, 2000; pp. 1-5.

Hiroshi Nakagawa, et al., Abstract, "Creation of Long Linear Transmural Radiofrequencey Lesions in Atrium Using a Novel Spiral Ribbon—Saline Irrigated Electrode Catheter," Journal of American College of Cardiology, Feb. 1996.

Taijiro Sueda, et al., "Efficacy of a Simple Left Atrial Procudure for Chronic Atrial Procedure for Chronic Atrial Fibrillation in Mitral Valve Operations," The Annals of Thoracic Surgery, 1997, vol. 63, pp. 1070-1073.

Re: Dr. Adam E. Saltman, New Program in Surgical Electrophysiology Established, Interet Website of Departmental News, Dept. of Surgery, University Hospital & Medical Center, Stony Brook State University of New York (www.informatics.synysb.edu/surgery/electro-news.html); 2000, pp. 1-2.

Mien-Cheng Chen, M.D., et al., "Radiofrequency and Cryoablation of Atrial Fibrillation in Patients Undergoing Valvular Operations," Anals of Thoracic Surgery, 1998:65:1666-1972.

Arif Elvan, M.D., et al., Abstract, "Radiofrequency Catheter Ablation of the Atria Reduces Inducibility and Duration of Atrial Fibrillation in Dogs," CIRCULATION, 1995:91:2235-2244.

Warren M. Jackman, M.D., et al., "Radiofrequency Current Directed Across the Mitral Anulus With a Bipolar Epicardial-Endocardial Catheter Electrode Configuration in Dogs," CIRCULATION, 1988; vol. 78, No. 5, pp. 1288-1297.

Lauren Neergaard, "Slicing a Heart to Make It Beat," Article from the Associated Press, Mar. 26, 1998 Website (www.nando.com/newsroom/ntn/health/032698/health24_22737_body.html).

James L. Cox, M.D., Ed., "Seminars in Thoracic and Cardiovascular Surgery: The Maze Procedure for Atrial Fibrillation," 2000, vol. 12, No. 1.

Yoshito Inoue, et al., "Video Assisted Thoracoscopic and Cardioscopic Radiofrequency Maze Ablation," ASAIO Journal, 1997, pp. 334-337.

Yoshito Inoue, et al., Abstract, "Video Assisted Thoracoscopic and Cardioscopic Radiofrequency Maze Ablation," ASAIO Journal, 1997.

Mary O. Palazzo, RN, MS, CCRN, "What You Need To Know—a-fib 101," from the Atrial Fibrillation Page Website (www.members.aol.com/mazern/afib101.htm) Jun. 5, 2000.

Mary O. Palazzo, RN, MS, CCRN, "What You Need To Know—maze FAQ," from the Atrial Fibrillation Page Website (www.members.aol.com/mazern/mazefaq.htm) Nov. 25, 1999.

Mary O. Palazzo, RN, MS, CCRN, "What You Need To Know—maze FAQ," from the Atrial Fibrillation Page Website (www.members.aol.com/mazern/mazefaq.htm) Jun. 21, 2000.

Stuart P. Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiololgy, 2000, vol. 35, No. 2, pp. 442-450.

Akira T. Kawaguchi, et al., "Factors Affecting Rhythm After the Maze Procedure for Atrial Fibrillation," Circulation, 1998; vol. 78, No. 5, pp. 1288-1296.

Ivan M. Robbins, M.D., et al., "Pulmonary Vein Stenosis After Catheter Ablation of Atrial Fibrillation," CIRCULATION, 1998; 98:1769-1775.

Enrique, J. Berjano, et al., "Bipolar Electrosurgery With Long Electrodes for RF Coagulation of Atrial Tissue," Proceedings 19th International Conference—IEEE/EMBS Oct. 30-Nov. 2, 1997 Chicago, Ill. USA, pp. 2528-2530.

Taijiro Sueda, et al., "Simple Left Atrial Procedure for Chronic Atrial Fibrillation Associated with Mitral Valve Disease," The Annals of Thoracic Surgery, 1996;62:1796-1800.

* cited by examiner

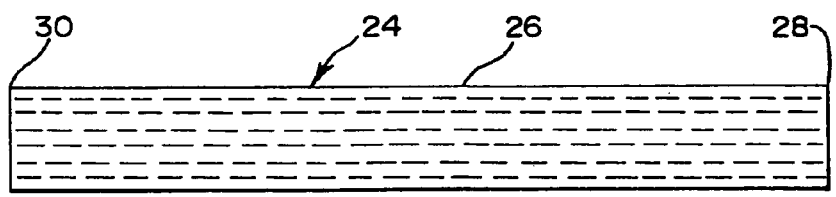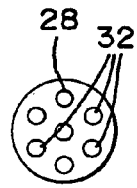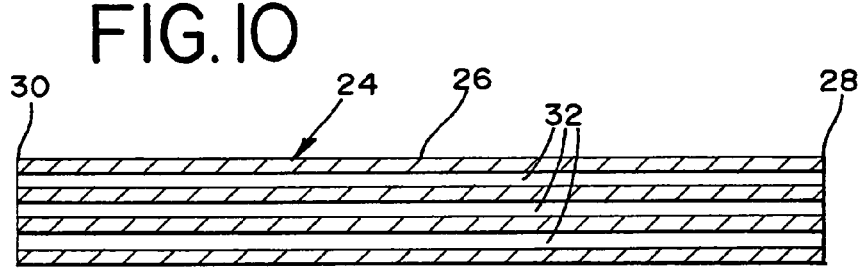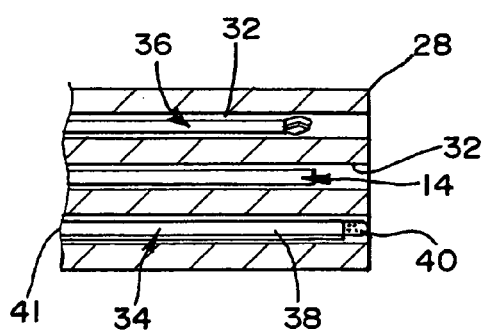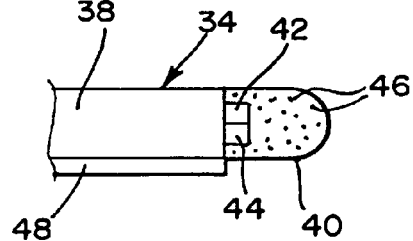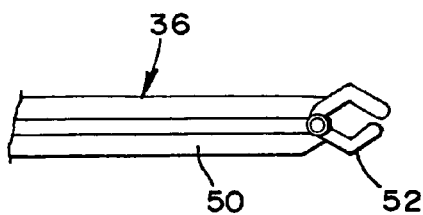

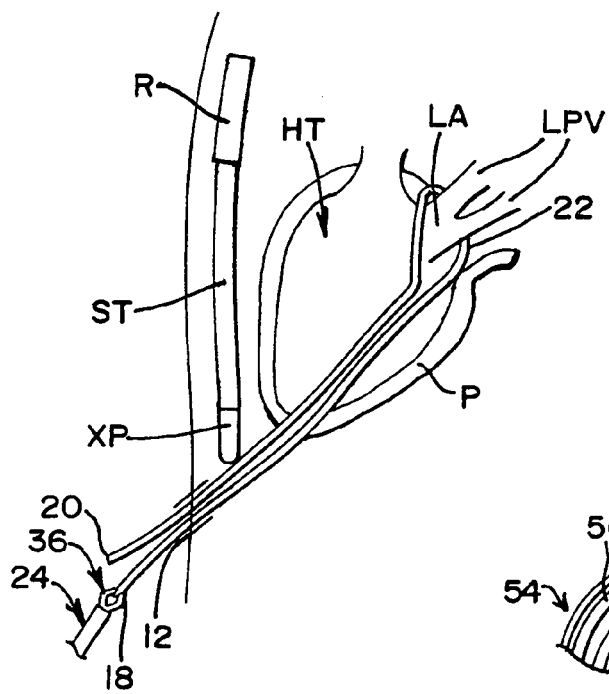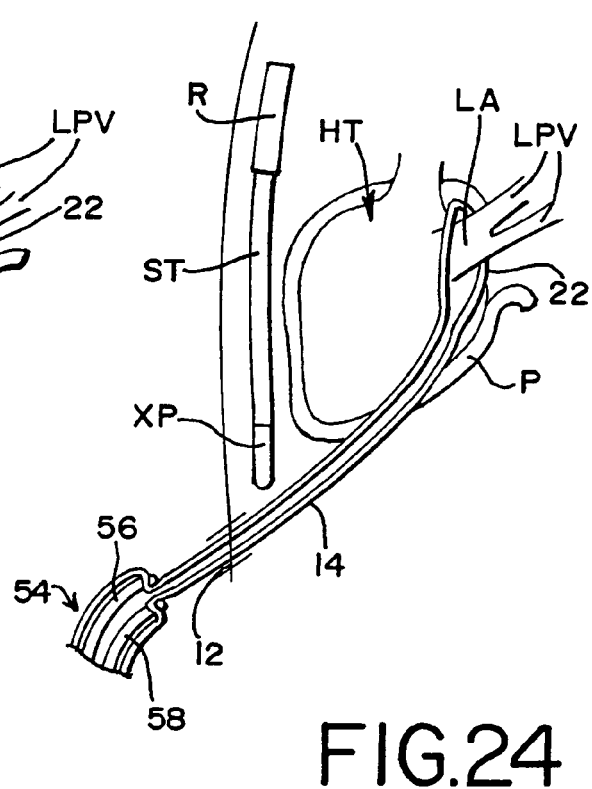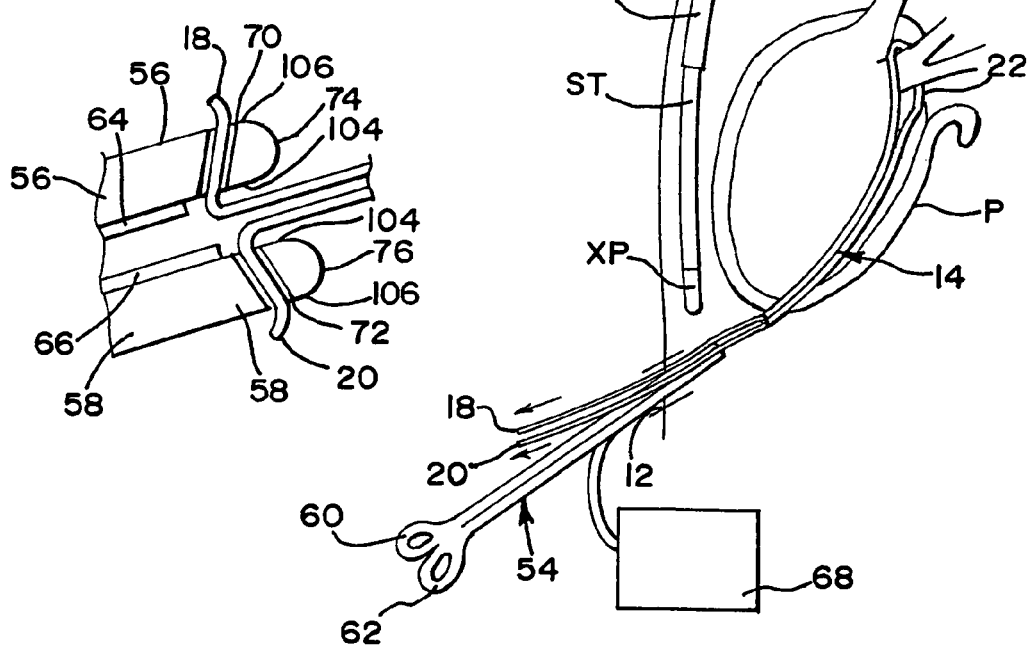

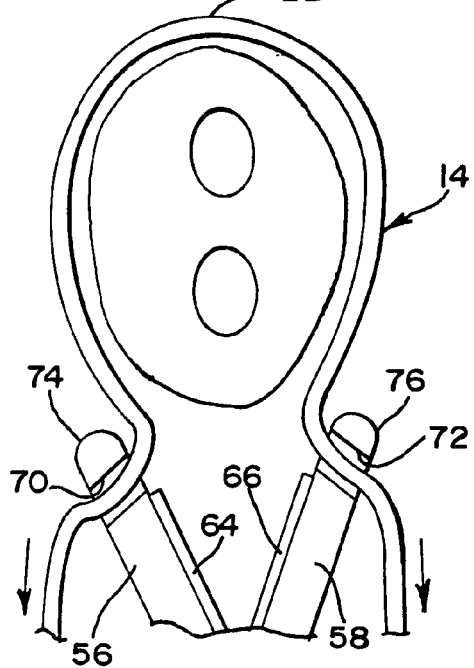
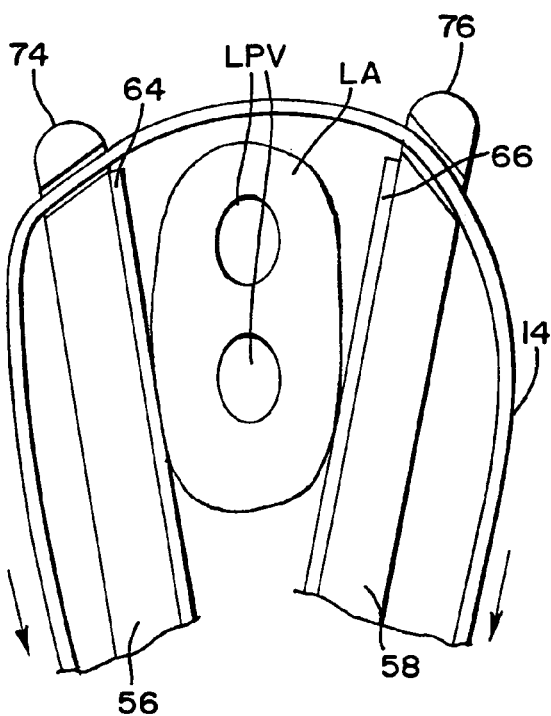
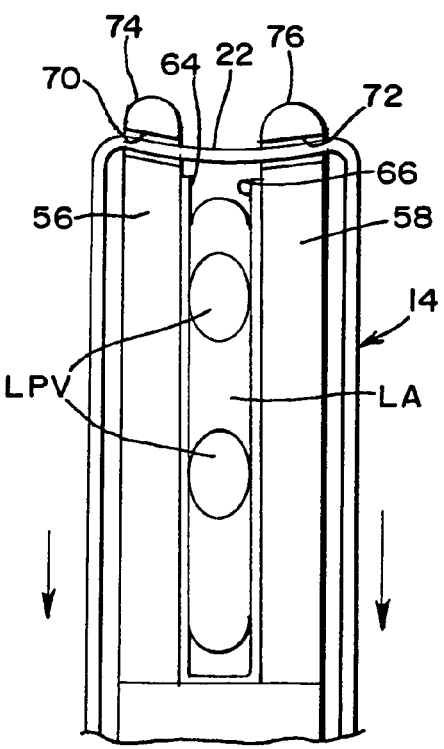
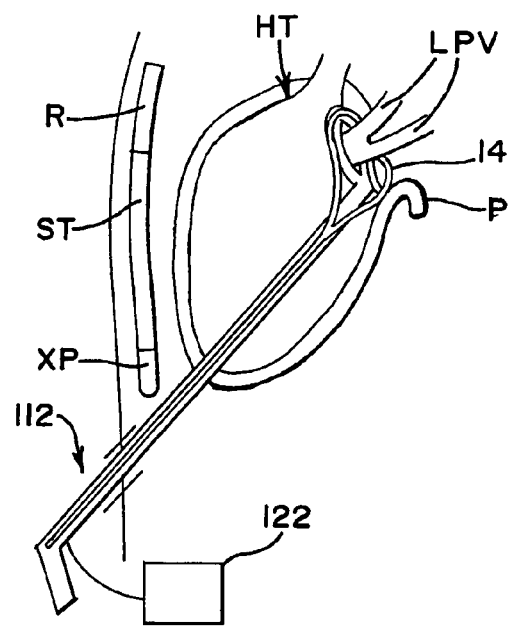

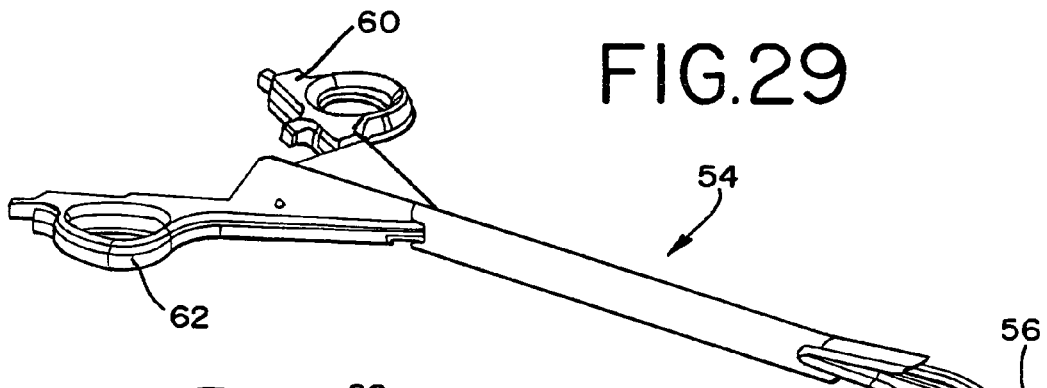
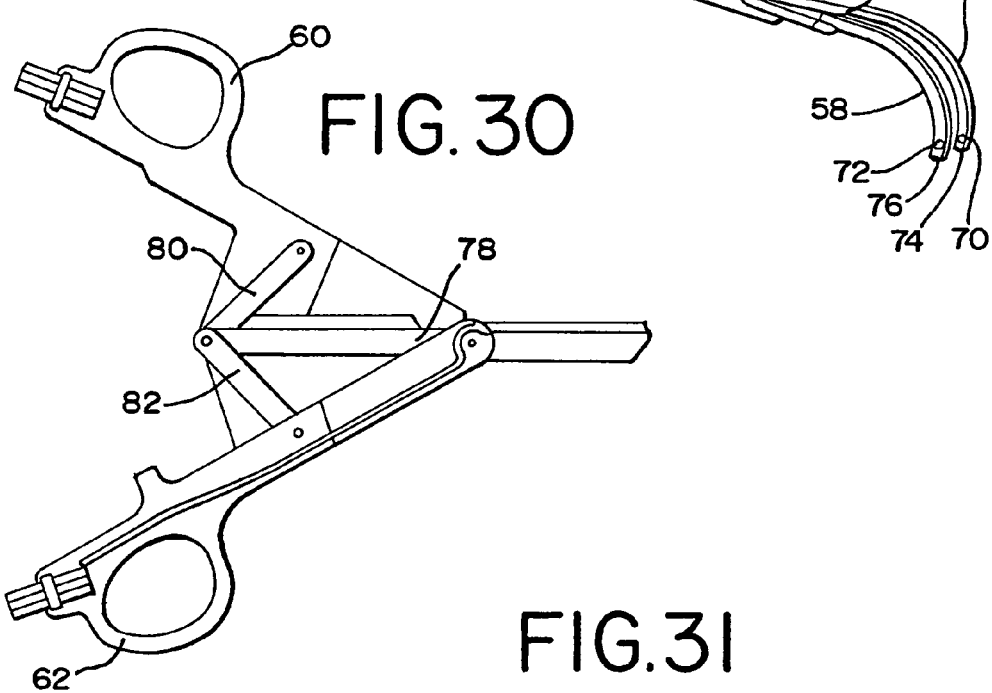
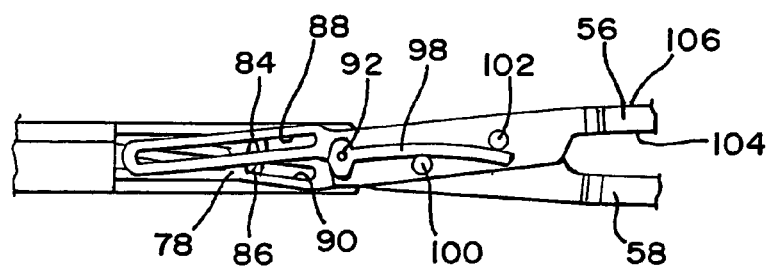
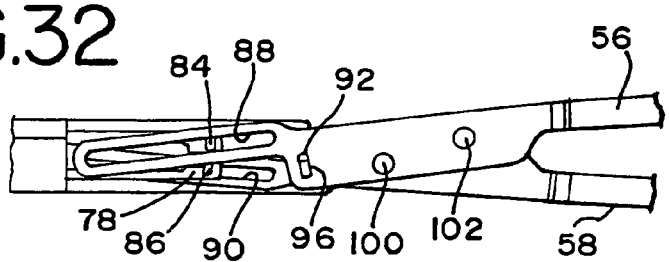

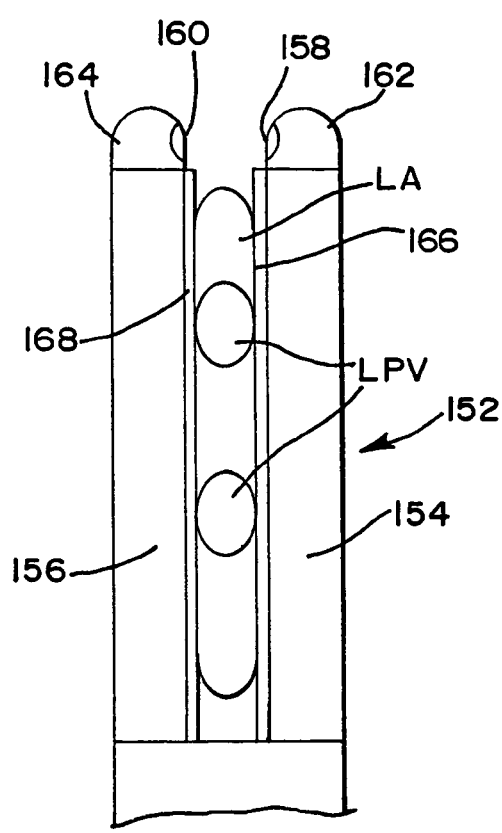
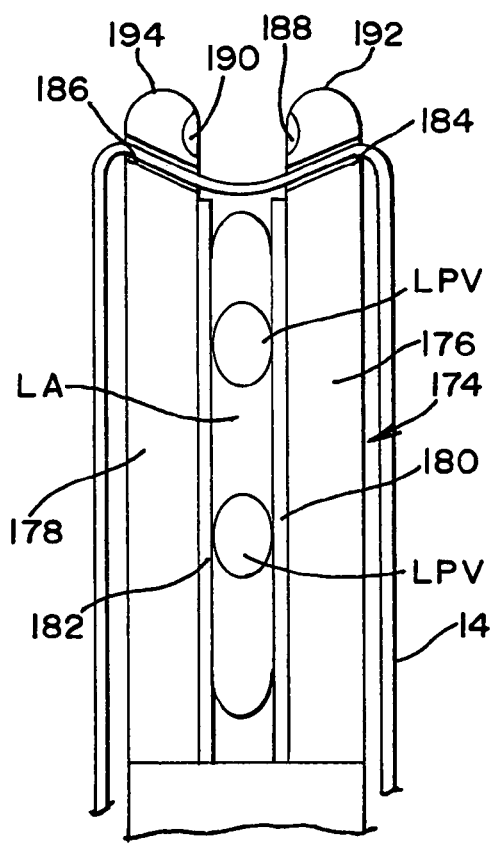
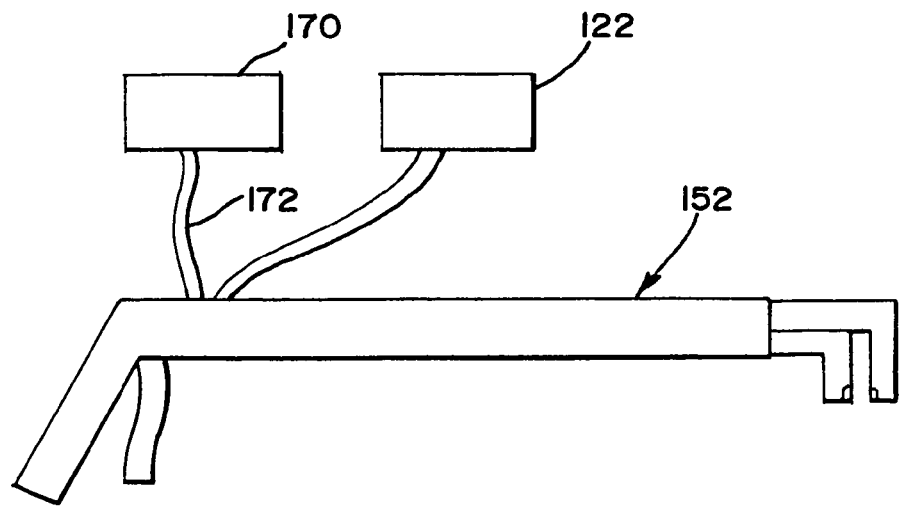

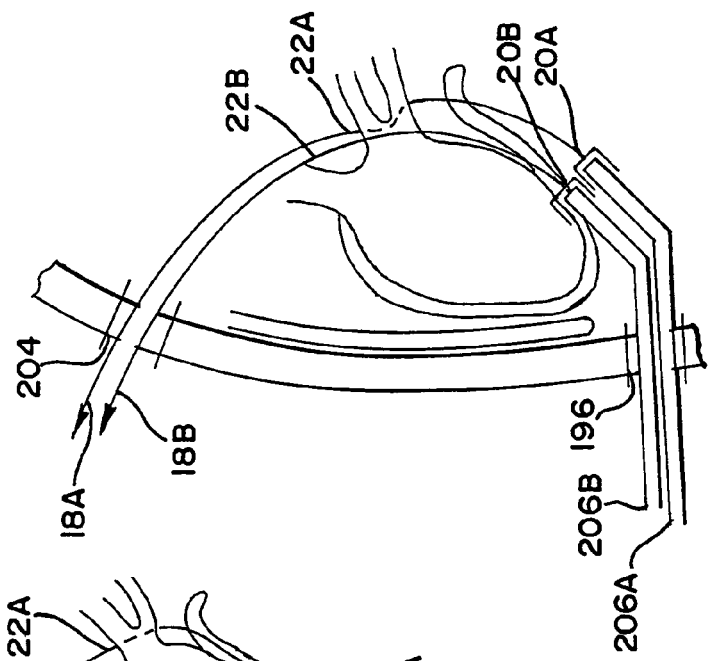
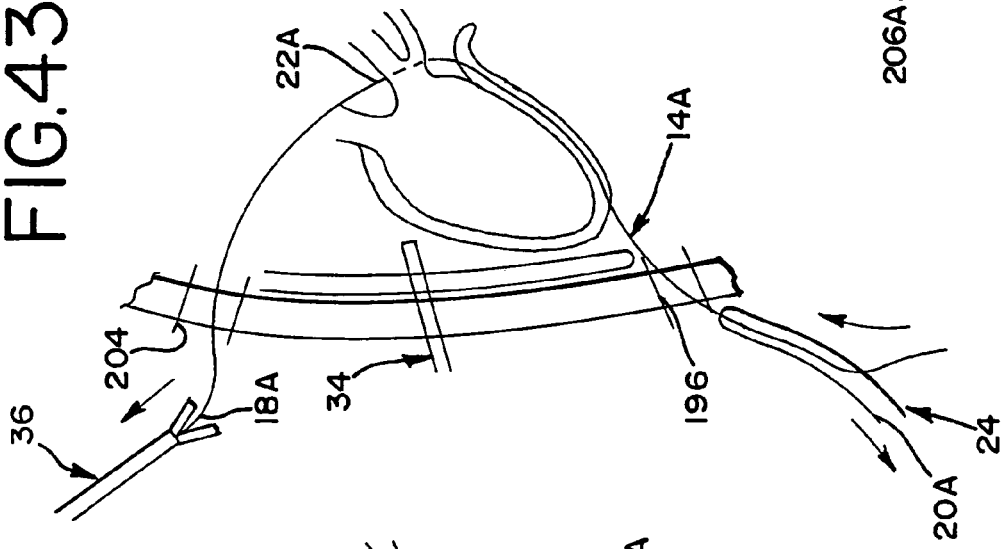
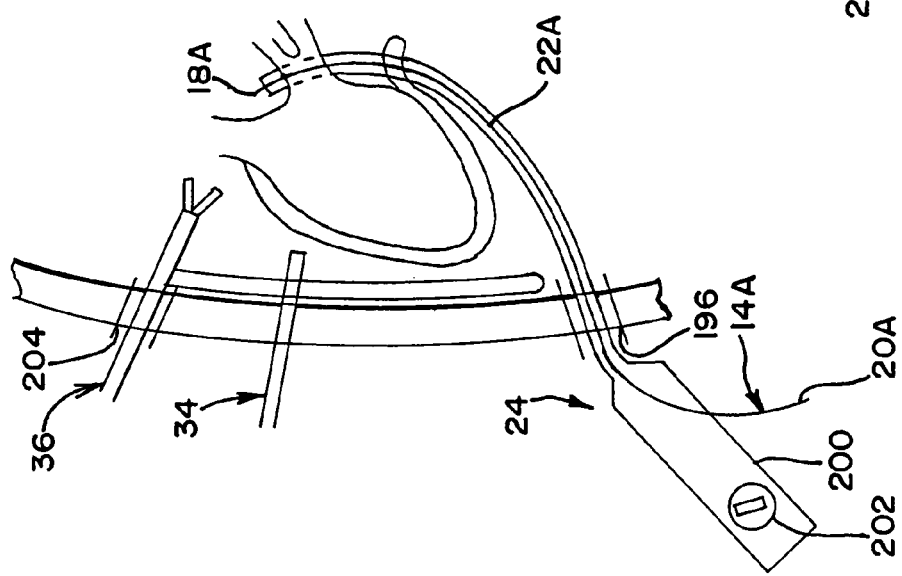

METHOD AND APPARATUS FOR ABLATING CARDIAC TISSUE WITH GUIDE FACILITY

This application is a non-provisional application which claims the benefit of provisional application Ser. Nos. 60/464,713, filed Apr. 23, 2003, and 60/547,364, filed Feb. 24, 2004, which applications are incorporated by reference herein.

BACKGROUND OF THE INVENTION

Atrial fibrillation is the most common heart arrhythmia in the world, affecting over 2.5 million people in the United States alone. Ablation of cardiac tissue, in order to create scar tissue that poses an interruption in the path of the errant electrical impulses in the heart tissue, is a commonly performed procedure to treat cardiac arrhythmias. Such ablation may range from the ablation of a small area of heart tissue to a series of ablations forming a strategic placement of incisions in both atria to stop the conduction and formation of errant impulses.

Ablation has been achieved or suggested using a variety of techniques, such as freezing via cryogenic probe, heating via RF energy, surgical cutting and other techniques. As used here, "ablation" means the removal or destruction of the function of a body part, such as cardiac tissue, regardless of the apparatus or process used to carry out the ablation. Also, as used herein, "transmural" means through the wall or thickness, such as through the wall or thickness of a hollow organ or vessel.

Ablation of cardiac tissue may be carried out in an open surgical procedure, where the breastbone is divided and the surgeon has direct access to the heart, or through a minimally invasive has direct access to the heart, or through a minimally invasive route, such as between the ribs, through a sub-xyphoid incision or via catheter that is introduced through a vein, and into the heart.

Prior to any ablation, the heart typically is electronically mapped to locate the point or points of tissue which are causing the arrhythmia. With minimally invasive procedures such as via a catheter, the catheter is directed to the aberrant tissue, and an electrode or cryogenic probe is placed in contact with the endocardial tissue. RF energy is delivered from the electrode to the tissue to heat and ablate the tissue (or the tissue may be frozen by the cryogenic probe), thus eliminating the source of the arrhythmia.

Common problems encountered in this procedure are difficulty in precisely locating the aberrant tissue, and complications related to the ablation of the tissue. Locating the area of tissue causing the arrhythmia often involves several hours of electrically "mapping" the inner surface of the heart using a variety of mapping catheters, and once the aberrant tissue is located, it is often difficult to position the catheter and the associated electrode or probe so that it is in contact with the desired tissue.

The application of either RF energy or ultra-low temperature freezing to the inside of the heart chamber also carries several risks and difficulties. It is very difficult to determine how much of the catheter electrode or cryogenic probe surface is in contact with the tissue since catheter electrodes and probes are cylindrical and the heart tissue cannot be visualized clearly with existing fluoroscopic technology. Further, because of the cylindrical shape, some of the exposed electrode or probe area will almost always be in contact with blood circulating in the heart, giving rise to a risk of clot formation.

Clot formation is almost always associated with RF energy or cryogenic delivery inside the heart because it is difficult to prevent the blood from being exposed to the electrode or probe surface. Some of the RF current flows through the blood between the electrode and the heart tissue and this blood is coagulated, or frozen when a cryogenic probe is used, possibly resulting in clot formation. When RF energy is applied, the temperature of the electrode is typically monitored so as to not exceed a preset level, but temperatures necessary to achieve tissue ablation almost always result in blood coagulum forming on the electrode.

Overheating or overcooling of tissue is also a major complication, because the temperature monitoring only gives the temperature of the electrode or probe, which is, respectively, being cooled or warmed on the outside by blood flow. The actual temperature of the tissue being ablated by the electrode or probe is usually considerably higher or lower than the electrode or probe temperature, and this can result in overheating, or even charring, of the tissue in the case of an RF electrode, or freezing of too much tissue by a cryogenic probe. Overheated or charred tissue can act as a locus for thrombus and clot formation, and over freezing can destroy more tissue than necessary.

It is also very difficult to achieve ablation of tissue deep within the heart wall. A recent study reported that to achieve a depth of ablation of 5 mm, it was necessary to ablate an area almost 8 mm wide in the endocardium. See, "Mechanism, Localization, and Cure of Atrial Arrhythmias Occurring After a New Intraoperative Endocardial Radiofrequency Ablation Procedure for Atrial Fibrillation," Thomas, et al., *J. Am. Coll. Cardiology*, Vol. 35, No. 2, 2000. As the depth of penetration increases, the time, power, and temperature requirements increase, thus increasing the risk of thrombus formation.

In certain applications, it is desired to obtain a continuous line of ablated tissue in the endocardium. Using a discrete or point electrode or probe, the catheter must be "dragged" from point to point to create a line, and frequently the line is not continuous. Multielectrode catheters have been developed which can be left in place, but continuity can still be difficult to achieve, and the lesions created can be quite wide.

Because of the risks of char and thrombus formation, RF energy, or any form of endocardial ablation, is rarely used on the left side of the heart, where a clot could cause a serious problem (e.g., stroke). Because of the physiology of the heart, it is also difficult to access certain areas of the left atrium via an endocardial, catheter-based approach.

Recently, epicardial ablation devices have been developed which apply RF energy to the outer wall of the heart to ablate tissue. These devices do not have the same risks concerning thrombus formation. However, it is still difficult to create long, continuous lesions, and it is difficult to achieve good depth of penetration without creating a large area of ablated tissue.

As noted above, other forms of energy have been used in ablation procedures, including ultrasound, cryogenic ablation, laser, and microwave technology. When used from an endocardial approach, the limitations of all energy-based ablation technologies to date are the difficulty in achieving continuous transmural lesions, and minimizing unnecessary damage to endocardial tissue. Ultrasonic and RF energy endocardial balloon technology has been developed to create circumferential lesions around the individual pulmonary veins. See e.g., U.S. Pat. No. 6,024,740 to Lesh et al. and U.S. Pat. Nos. 5,938,660 and 5,814,028 to Swartz et al. However, this technology creates rather wide (greater than 5 mm) lesions which could lead to stenosis (narrowing) of the pulmonary veins. See, "Pulmonary Vein Stenosis after Catheter Ablation of Atrial Fibrillation," Robbins, et al., *Circulation*, Vol. 98, pages 1769-1775, 1998. The large lesion area can also act as a locus point for thrombus formation. Additionally, there is no feedback to determine when full transmural ablation has been achieved. Cryogenic ablation has been attempted both endocardially and epicardially (see e.g., U.S. Pat. Nos. 5,733,280 to Avitall, 5,147,355 to Friedman et al., and 5,423,807 to Milder, and WO 98/17187, the latter disclosing an angled cryogenic probe, one arm of which is inserted into the interior of the heart through an opening in the heart wall that is hemostatically sealed around the arm by means of a suture or staples), but because of the time required to freeze tissue, and the delivery systems used, it is difficult to create a continuous line, and uniform transmurality is difficult to verify.

Published PCT applications WO 99/56644 and WO 99/56648 disclose an endocardial ablation catheter with a reference plate located on the epicardium to act as an indifferent electrode or backplate that is maintained at the reference level of the generator. Current flows either between the electrodes located on the catheter, or between the electrodes and the reference plate. It is important to note that this reference plate is essentially a monopolar reference pad. Consequently, there is no energy delivered at the backplate/tissue interface intended to ablate tissue. Instead, the energy is delivered at the electrode/tissue interface within the endocardium, and travels through the heart tissue either to another endocardial electrode, or to the backplate. Tissue ablation proceeds from the electrodes in contact with the endocardium outward to the epicardium. Other references disclose epicardial multielectrode devices that deliver either monopolar or bipolar energy to the outside surface of the heart.

It is important to note that all endocardial ablation devices that attempt to ablate tissue through the full thickness of the cardiac wall have a risk associated with damaging structures within or on the outer surface of the cardiac wall. As an example, if a catheter is delivering energy from the inside of the atrium to the outside, and a coronary artery, the esophagus, or other critical structure is in contact with the atrial wall, the structure can be damaged by the transfer of energy from within the heart to the structure. The coronary arteries, esophagus, aorta, pulmonary veins, and pulmonary artery are all structures that are in contact with the outer wall of the atrium, and could be damaged by energy transmitted through the atrial wall.

Several devices and methods utilizing ablation in the treatment of atrial fibrillation have been described in co-pending applications to the current inventor: Ser. No. 10/038,506, filed Nov. 9, 2001, which is a continuation-in-part of application Ser. No. 10/032,378, filed Oct. 26, 2001, now U.S. Pat. No. 6,932,811, which is a continuation-in-part of application Ser. No. 09/844,225 filed Apr. 27, 2001, now U.S. Pat. No. 6,517,536, which is a continuation-in-part of application Ser. No. 09/747,609 Dec. 22, 2000, now U.S. Pat. No. 6,546,935, which claims the benefit of provisional application Ser. No. 60/200,072, filed Apr. 27, 2000. These applications are hereby incorporated by reference in the present application.

Accordingly, it is the object of the present invention to provide an improved method and apparatus for making transmural ablations to heart tissue.

It is a related object to provide a method and apparatus for making transmural ablation in heart tissue that minimizes unnecessary damage to the heart tissue.

It is a further object to provide a method and apparatus for making transmural ablation in heart tissue that creates continuous lesions in a single step.

It is further an object to provide a method and apparatus for guiding the ablation instrument to a selected cardiac location prior to ablation.

It is also an object to provide a method and apparatus for engaging cardiac tissue at a selected cardiac location.

It is still a further object to provide a method and apparatus for ablating cardiac tissue which utilizes a sub-xyphoid approach.

SUMMARY OF THE INVENTION

These objects, and others will become apparent upon reference to the following detailed description and attached drawings are achieved by the use of an apparatus for ablating cardiac tissue. The apparatus includes an elongated body having a distal end, a proximal end, and first and second jaws carried at the distal end. The first and second jaws are moveable between a spaced apart open position and a closed position. Each jaw comprises an ablating element connected to an ablation source for ablating cardiac tissue between the jaws. Each jaw further includes a channel which is distally located in relation to the ablation element. A flexible elongated guide facility has first and second ends and an intermediate portion extending between the first and second ends. Upon positioning of the intermediate portion around a selected cardiac location, each end of the guide facility is slidably received within a separate channel of the jaws so as to guide the jaws to the selected cardiac location for ablation thereof.

The method achieved by the use of the apparatus and includes the steps of making a percutaneous incision to define an instrument receiving passage. The method is performed using the flexibly elongated guide and an ablation instrument having at least a pair of relatively moveable jaws, similar to that described above. The first end of the guide facility is introduced through the instrument receiving passage to a selected cardiac location adjacent one of the right and left pulmonary veins. The guide facility is advanced to, preferably around, the selected cardiac location such that the intermediate portion of the guide facility engages the selected cardiac location. Then the first end of the guide facility is extended or withdraw to a position disposed outside the instrument receiving passage such that first and second ends of the guide facility are positioned outside the instrument receiving passage and the intermediate portion engages the selected cardiac location. Each of the jaws of the ablation instrument is cooperatively engaged with a separate one of the ends of the guide facility. The ablation instrument is inserted through the instrument receiving passage and guided with the aid of the guide facility to the selected cardiac location such that the cardiac tissue at the selected location is disposed between the jaws. The cardiac tissue at the selected location is ablated.

The method and apparatus may be modified so as to be performed using multiple guide facilities. Each guide facility including first and second ends and an intermediate portion extending between the respective ends. By way of example and not limitation, a method and apparatus for using two guide facilities is shown and described. A first end of a first guide facility is inserted into the instrument receiving passage, which may be, and preferably is, accessed via a first sub-xyphoid incision. The first guide facility is advanced to a selected location and then the first end is extended past the selected location to a position outside of the patient through a second incision which provides access to the instrument receiving passage preferably through an intercostal or between-the-ribs incision. The intermediate portion of the first guide facility preferably engages one side of the selected tissue to be ablated. A second guide facility is placed within the patient's chest and follows the same instrument receiving passage between the two incisions except that the second guide facility preferably engages another side of the selected tissue. One end of each guide facility preferably engages a separate jaw of the ablation instrument so as to position the jaws on the sides of the tissue to be ablated. A locating instrument and/or grasper may be used to facilitate visualization or dissection of tissue around the selected location and/or to provide tension to any of the guide facilities prior to or during placement thereof.

BRIEF DESCRIPTION OF THE DRAWINGS

FIG. 8 is a plan view of a locating instrument.

FIG. 9 is a end view of the locating instrument.

FIG. 10 is a sectional view of the locating instrument.

FIG. 11 is an enlarged sectional view of one end of the locating instrument with various instruments disposed within passageways.

FIG. 12 is an enlarged view of a distal end of an endoscope.

FIG. 13 is a plan view of a grasping instrument.

FIG. 21 is a cross-sectional side elevation view of a patient's chest illustrating the step of extending the first end of the guide facility to a position disposed outside the instrument receiving passage.

FIG. 22 is a cross-sectional side elevation view of a patient's chest illustrating the step of cooperatively engaging each of the jaws of a first embodiment of the ablation instrument with a separate one of the ends of the guide facility.

FIG. 23 is an enlarged sectional view of the distal ends of an ablation instrument.

FIG. 24 is cross-sectional side-elevation view of a patient's chest illustrating the step of inserting the ablation instrument through the instrument receiving passage.

FIGS. 25-27 are enlarged posterior views of the left atrium and left pulmonary veins sequentially illustrating the step of guiding the ablation instrument with the aid of the guide facility to the selected cardiac location and the step of ablating the cardiac tissue at the selected location.

FIG. 28 is a cross-sectional side elevation view of a patient's chest illustrating the step of ablating the cardiac tissue at a selected location using a second embodiment of the ablation instrument.

FIG. 29 is a perspective view of the first embodiment of the ablation instrument.

FIG. 30 is an enlarged plan view of the handle position of the ablation instrument of FIG. 29, with portions removed to show detail.

FIGS. 31 and 32 are enlarged plan views of the jaw actuation mechanism for the ablation instrument of the FIG. 29.

FIG. 39 is an enlarged posterior view of the left atrium and left pulmonary veins illustrating the step of ablating the selected cardiac location using the ablating instrument of FIG. 37.

FIG. 40 is a side view of the ablating instrument shown in FIG. 37.

FIG. 41 is an enlarged posterior view of the left atrium and left pulmonary vein illustrating the step of ablating the selected cardiac location using a fourth embodiment of the ablating instrument and including the guide facility.

FIG. 42 is a cross-sectional side view of a patient's chest illustrating another embodiment of the method and apparatus showing multiple guide facilities, and showing the steps of introducing a guide facility into the chest employing a sub-xyphoid approach and advancing the guide facility to a posterior heart location, in particular showing, the vicinity of a pair of pulmonary veins.

FIG. 43 is a cross-sectional side view of a patient's chest showing the step of extending the guide facility, as shown in FIG. 42, to a location outside of the patient's chest via an incision through the ribs.

FIG. 44 is a cross-sectional side view of a patient's chest showing another guide facility being inserted into the patient's chest via a sub-xyphoid approach, engaging cardiac tissue and extended to a location outside the patient via an intercostal incision, similar to the guide facility shown in FIGS. 42-43.

DETAILED DESCRIPTION OF THE PREFERRED EMBODIMENTS

The present invention provides a method and apparatus for ablating cardiac tissue of the heart. Although the method for ablation will be described by way of example but not limitation in relation to the atrial tissue adjacent one of the right and left pulmonary veins, ablation of other areas of the heart are also possible.

Figure 1:
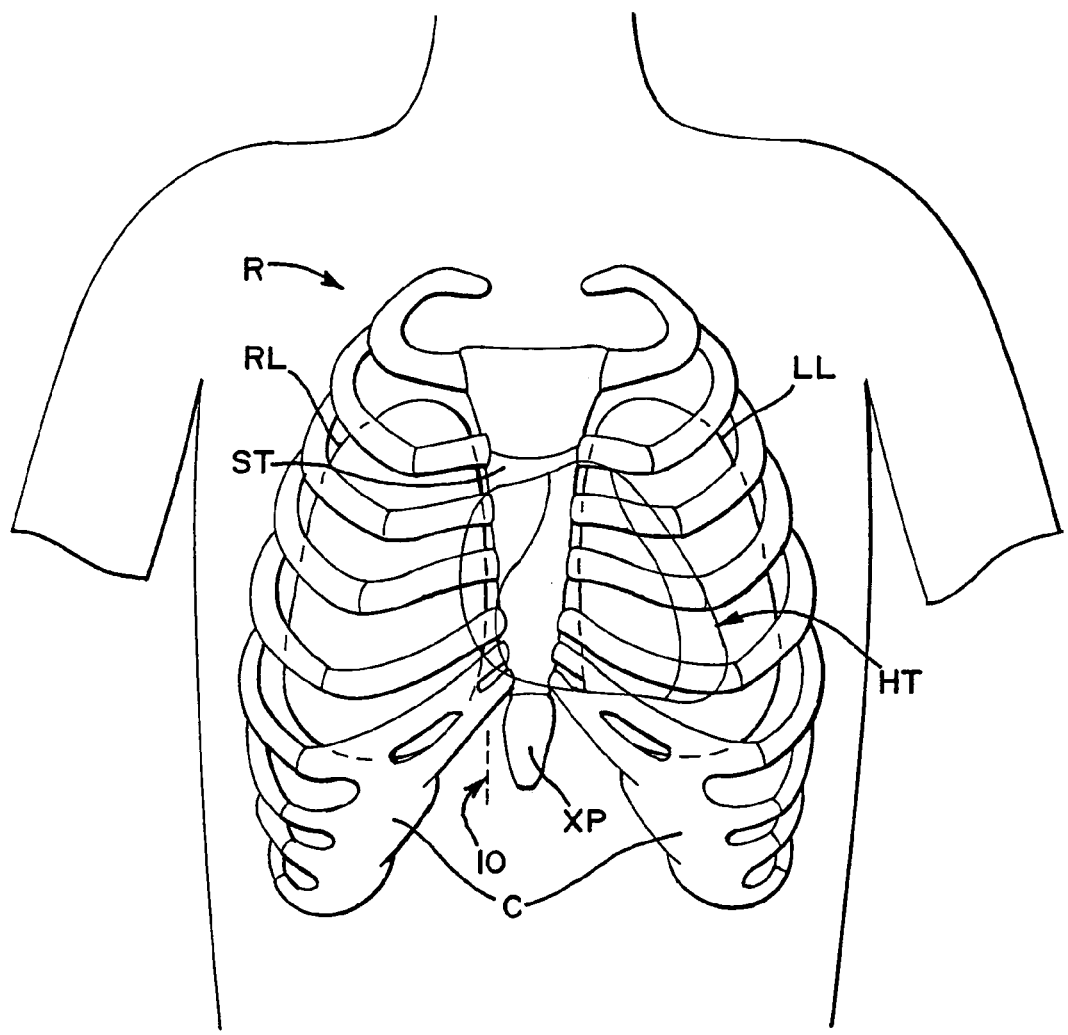
FIG. 1 shows an anterior plan view of the heart, the chest cavity and an access location for performing ablation.

As shown in FIG. 1 an incision 10 is made into the patient. The incision in FIG. 1 is shown in the xyphoid region of the patient. Although the method of the present invention is performed via a sub-xyphoid approach to ablate cardiac tissue, it is realized that other approaches may be utilized without departing from the scope of the claimed invention such as, for example, intercostal and intravenous and other minimally invasive approaches as well as more invasive approaches such as open chest procedures or approaches which remove all or a portion of the rib cage. FIG. 1 illustrates a patient's chest including a rib cage R, sternum ST, xyphoid XP, coastal cartilage C, right lung RL, left lung LL and heart HT. The incision may be performed by one of several medical instruments 11 such as a scalpel or the like. Once the incision is made, the opening defines an instrument receiving passage 12, as shown in FIGS. 14-17, which allows for access to the heart HT for ablation.

Figure 2:
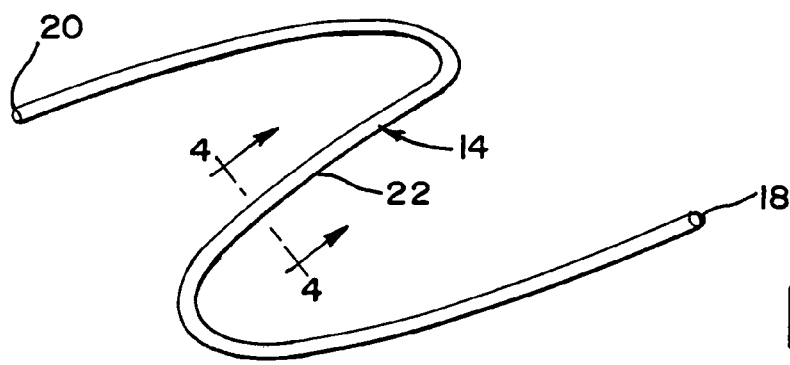
FIG. 2 is a perspective view of the guide facility.
Figure 7A:
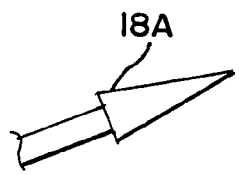
FIGS. 7A-7D illustrate alternative embodiments of a first end of the guide facility.
Figure 7B:
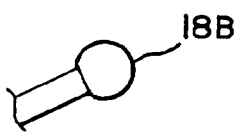
Figure 3:
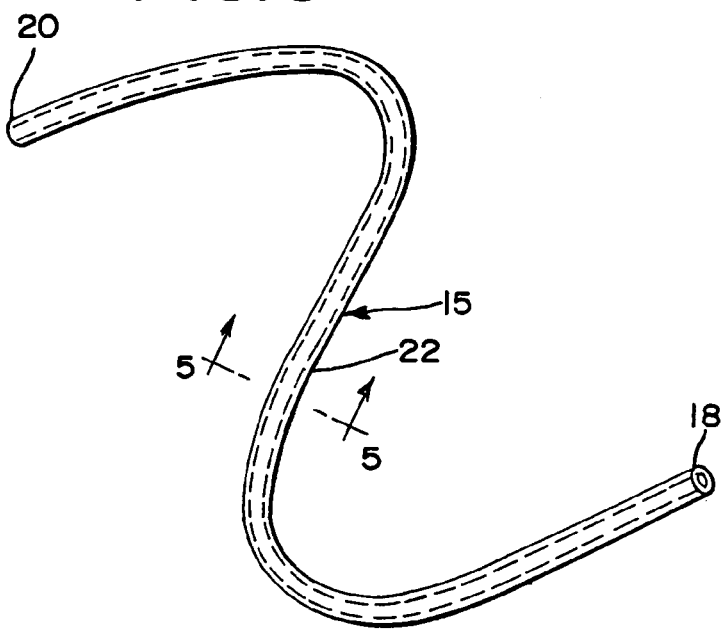
FIG. 3 is a perspective view of a second embodiment of the guide facility.
Figure 7C:
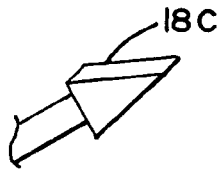
Figure 7D:
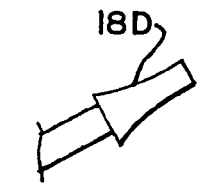
Figure 4:
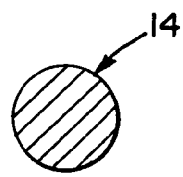
FIG. 4 is a sectional view taken along line 4-4 of FIG. 2.
Figure 5:
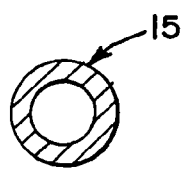
FIG. 5 is a sectional view taken along line 5-5 of FIG. 3.
Figure 6:
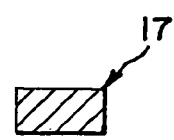
FIG. 6 shows a sectional view of the guide facility in accordance with the third aspect of the invention.
Figure 14:
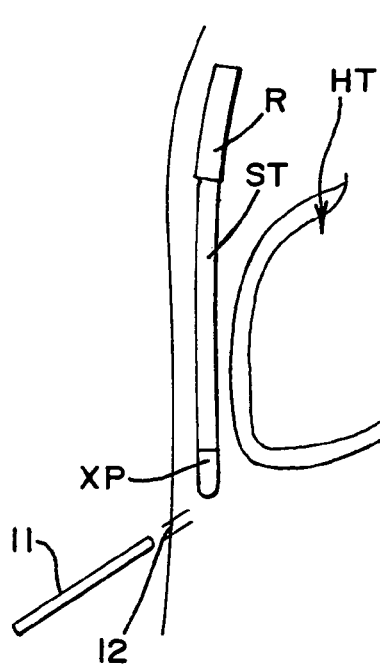
FIG. 14 is a cross-sectional side elevation view of a patient's chest illustrating the step of making a percutaneous incision to define an instrument receiving passage.

FIG. 2 illustrates a guide facility, generally at 14, for insertion into the instrument receiving passage 12. The guide facility 14 includes an elongated body 16, a first end 18, a second end 20 and an intermediate portion 22 which extends between the first end and the second end. The guide facility is generally made of a flexible material to facilitate positioning of the guide facility into the patient for placement around the cardiac tissue selected for ablation. Several types of guide facilities are possible including but not limited to a wire, a tube, surgical tape, or the like. For example, FIG. 3 illustrates a second embodiment of the guide facility 15, with like parts shown with like number, where the guide facility has an elongated tubular shape. Thus, it can be seen that the cross-sectional shape of the guide facility may be circular, as shown in FIG. 4, such as where the guide facility is a wire, or it may be tubular, as shown in FIG. 5, such as where the guide facility is a tube. A third embodiment of the guide facility 17 is in the form of surgical tape, the guide facility may have a non-circular cross section such as that shown in FIG. 6. As shown in FIGS. 7A-7D, it is possible that one or both ends of the guide facility 14 may have varying shapes for assisting introduction of the guide facility through the instrument receiving passage 12 and placement of the guide facility at the selected cardiac location such as, by way of example, a conical or frustoconical end 18A, a spherical or circular end 18B, a pyramidal end 18C, and a concave-sided end 18D.

Figure 15:
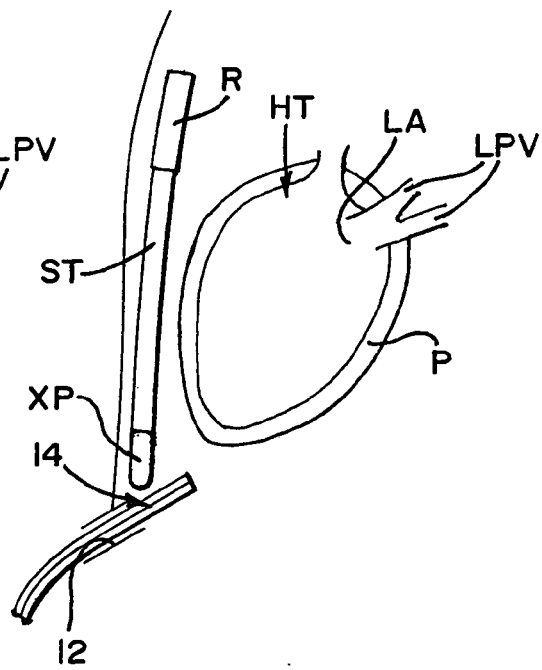
FIGS. 15-17 are cross-sectional side elevation views of the patient's chest sequentially illustrating the step of introducing the guide facility through the instrument receiving passage and the step of advancing the guide facility to the selected cardiac location.
Figure 16:
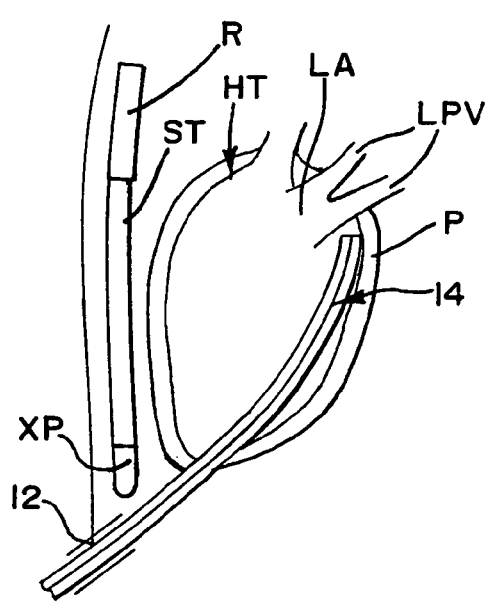
Figure 17:
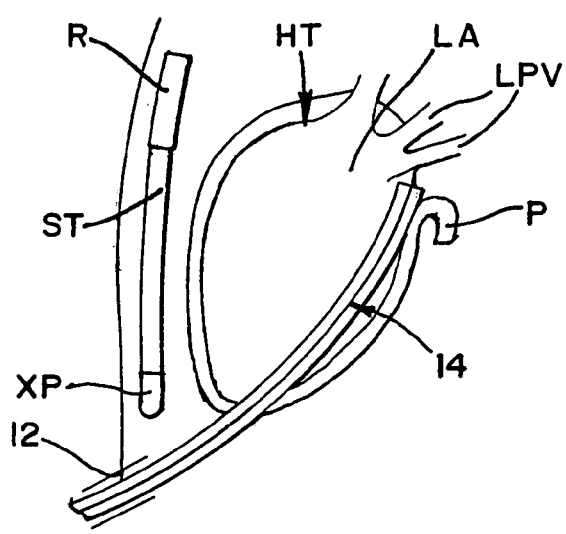

FIGS. 15-18 illustrate the first end 18 of the guide facility 14 being introduced through the instrument receiving passage 12 to the selected cardiac location. As shown in FIGS. 15-18, the selected cardiac location is shown at the left atrium LA adjacent the left pulmonary veins LPV. FIG. 15 shows the guide facility being introduced through the instrument receiving passage 12. In FIG. 16 the guide facility 14 is advanced to the selected cardiac location at the left atruim LA. FIG. 17 illustrates insertion of the first end 18 of the guide facility 14 into the intrapericardial space after an incision has been made into the pericardium P.

FIGS. 8-13 illustrate a locating instrument, generally at 24, which may be, and preferably is, used in combination with the guide facility 14 to locate the selection cardiac location and aid in introducing and advancing the guide facility. In FIGS. 8-13 the locating instrument 24 includes an elongated body 26, a distal end 28, and a proximal end 30 and defines a plurality of passageways 32. The guide facility 14 is inserted into one of the passageways 32 of the locating instrument 24 prior to introducing the guide facility into the patient. The combined locating instrument 24 and guide facility 14 is inserted into the patient through the instrument receiving passage 12 and advanced to the selected cardiac location, similar to the steps shown in FIGS. 15-18. The first end 18 of the guide facility 14 is adapted to extend beyond or forward of the distal end 28 of the locating instrument 24 and this extension may be aided by a wire, spring mechanism, actuating linkage (not shown) and or other actuation methods apparent to one skilled in the art.

As shown in FIG. 11, the passageways 32 of the locating instrument 24 also may receive other instruments such as an endoscope, generally at 34, a grasper, generally at 36, as well as other instruments. The passageways of the locating instrument may be reduced to a 2-5 mm diameter or less for insertion of the instruments and guide facility. Identifying and locating the cardiac tissue at the selected cardiac location may be performed by the endoscope 34, a viewing instrument or the like which is received within one or more of the passageways 32. FIGS. 11-12 show the endoscope 34 which is insertably received within one of the passageways 32 of the locating instrument 24, although it is also possible that the endoscope or other visualization device may be embedded within the locating instrument or formed integrally therewith. The endoscope 34 includes an elongated member 38 having a distal end 40 and a proximal end 41. The distal end 40 of the endoscope 34 may be adapted to extend beyond the distal end 28 of the locating instrument 24 and is preferably made of clear or transparent material so as to allow viewing of cardiac tissue. In FIG. 12, the distal end 40 of the endoscope includes visualization devices such as a lens 42 and a light 44 for viewing the heart HT and is connected to a viewing device (not shown) located outside of the patient through connecting wires embedded within the elongated member 38 of the endoscope 34. Irrigation ports 46 may be defined within the distal end 40 of the endoscope 34, which ports are fluidly connected to a fluid source (not shown) at the proximal end 41, and an elongated tube 48 supplies the fluid to the ports. As an alternative or in addition to the fluid supplied by the endoscope, one of the passageways 32 may be configured to allow for transmission of a fluid from the same or separate fluid source which is fluidly connected to the passageway 32 at the proximal end 30 of the locating instrument 24. Any type of fluid may be used, preferably saline.

Figure 18:
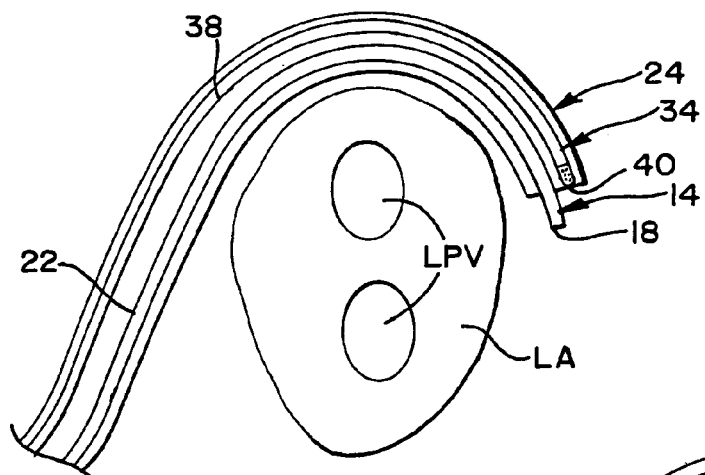
FIGS. 18-20 illustrate an enlarged posterior view of the left atrium and left pulmonary veins illustrating the step of advancing the guide facility to the selected cardiac location such that the intermediate portion engages the selected cardiac location.
Figure 19:
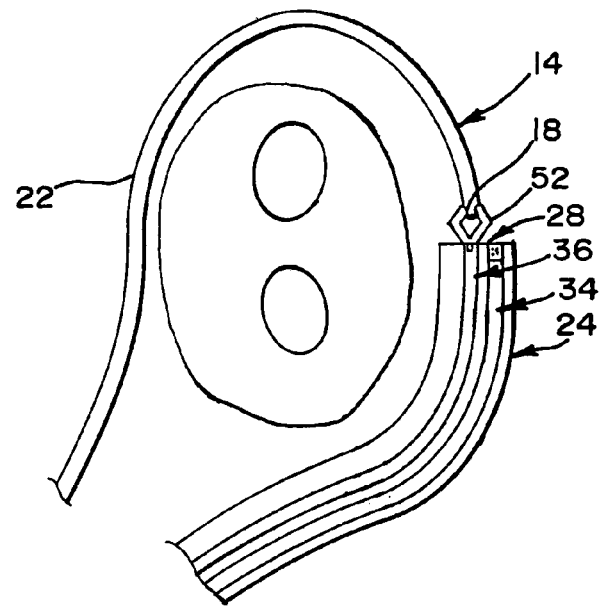

The endoscope 34 together with the locating instrument 24 may assist in locating the cardiac tissue for ablation by dissecting cardiac tissue. FIGS. 18-19 show the endoscope dissecting around the left atrial tissue adjacent the left pulmonary veins LPV. In FIG. 18, the endoscope dissects cardiac tissue at the left atrium LA adjacent the superior left pulmonary vein LPV. The endoscope is advanced together with the locating instrument 24 and the guide facility 14 around the top or the superior surface of the left atrium towards the posterior surface of the heart. During dissection, the endoscope clears the operative field and creates a working and viewing space. If fluid is used, insufflation of the fluid aids in dissection of the cardiac tissue and facilitates in the creation of a working and viewing space adjacent the selection cardiac location. The first end 18 of the guide facility 14 is then advanced forward of the distal end 28 of the locating instrument 24. The locating instrument 24 together with the endoscope 34 is withdrawn anteriorly while the guide facility remains positioned adjacent a posterior surface of the left atrium LA adjacent the left pulmonary veins LPV. In FIG. 19, the locating instrument 24 and the endoscope 34 is repositioned to dissect cardiac tissue at the left atrium LA adjacent the inferior left pulmonary vein LPV. The guide facility may be disengaged or withdrawn from the passageway 32 of the locating instrument 24 prior or subsequent to repositioning of the locating instrument 24. Other dissection approaches are also possible. For example, dissection may be performed at the lower or inferior surfaces of the left atrium LA before dissection of the upper or superior surface of the left atrium. Although it is preferred that the locating instrument 24 and/or endoscope 34 may perform dissection first in one direction around the selected cardiac location and then in another direction which is generally opposite to the first direction, other approaches may be used without departing from the scope of the invention.

Figure 20:
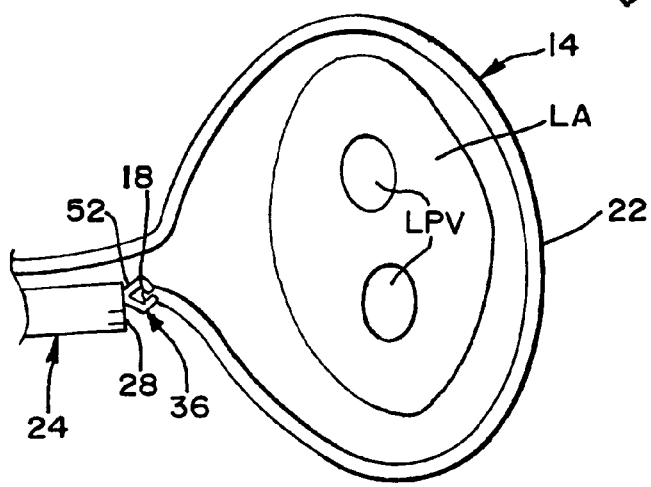

Once the first end 18 of the guide facility 14 has been advanced to the selected cardiac location, such as the left atrium LA adjacent the left pulmonary veins LPV in FIGS. 18-19, the first end 18 of the guide facility is advanced around the base of the left pulmonary veins LPV to engage the selected cardiac location. As shown in FIGS. 19-20, this is performed preferably by pulling the first end 18 of the guide facility around the selected cardiac location with the aid of the grasper 36. The grasper 36 includes a body 50 and a distal grasping portion 52. The grasper 36 may be positioned in one of the passageways 32 of the locating instrument 24 and adapted to extend from the distal end 28 of the locating instrument so as to engage the first end 18 of the guide facility 14. As shown in FIG. 19, the distal grasping portion 52 engages the first end 18 of the guide facility, preferably in a clamping arrangement, and may be actuated by a linkage which is disposed within the locating instrument 24 and actuated at the proximal end 30 thereof.

Once the distal grasping portion 52 engages the first end 18 of the guide facility, the grasper 36 together with the locating instrument 24 may be withdrawn so as to pull the guide facility 14 around the selected cardiac location as shown in FIG. 20. In this way, the intermediate portion 22 of the guide facility 14 is disposed to engage the selected cardiac location and in fact is positioned circumferentially around the selected cardiac location. As shown in FIG. 21, the locating instrument 24 together with the grasper 36 are withdrawn through the instrument receiving passage 12. The distal grasping portion 52 of the grasper 36 and the first end 18 of the guide facility 14 remain in a clamping engagement so that when the locating instrument 24 and the grasper 36 are withdrawn through the instrument receiving passage 12, the first end of the guide facility is also withdrawn through the instrument receiving passage. So the guide facility is disposed partially outside and partially inside the patient chest with the first and second ends 18, 20 of the guide facility 14 positioned outside the instrument receiving passage 12 and the intermediate portion 22 of the guide facility engaging the selected cardiac location within the chest of the patient.

Figure 33:
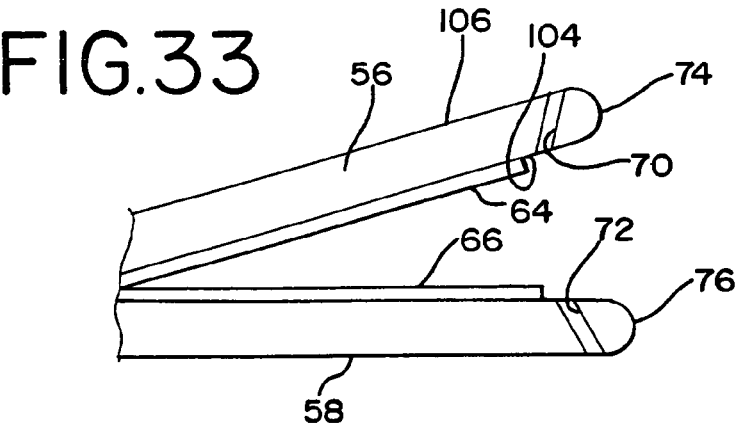
FIG. 33 is an enlarged plan view of the jaws of the ablation instrument of FIG. 29.
Figure 34:
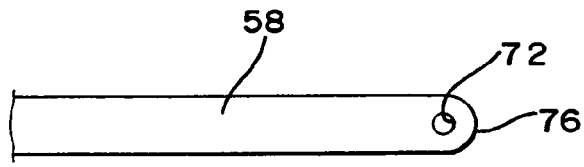
FIG. 34 is enlarged side view of the jaws of the ablation instrument of FIG. 29.
Figure 37:
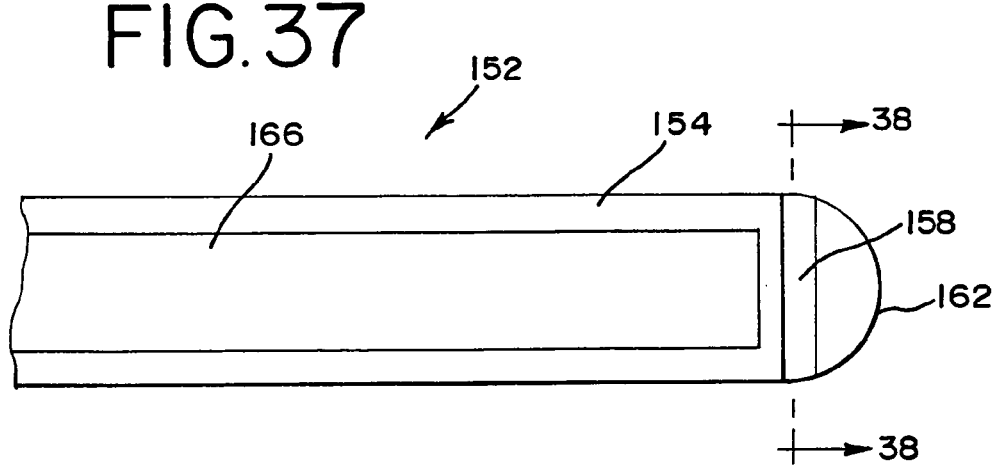
FIG. 37 is an enlarged partial view of an inside of a jaw assembly of a third embodiment of the ablating instrument.

FIGS. 22-27 illustrate positioning of an ablation instrument, generally designated at 54, and ablation of the selected cardiac location using the ablation instrument. The ablation instrument 54 is of the type shown in FIGS. 29-34 and includes first and second jaws 56 and 58, respectively, and first and second handle members 60 and 62, respectively. Each jaw 56, 58 may be straight or curved. The jaws 56, 58 define a working portion which may be between approximately 3-8 centimeters in length. The two handle members 60, 62 define ring handles which are joined together for actuation of the ablation instrument 54. As best seen in FIG. 23, each jaw includes an ablating element 64, 66 and each ablating element is connected to an ablation source 68, indicated in FIG. 24. As set forth in the application issuing as U.S. Pat. No. 6,932,811, incorporated by reference above, RF energy of opposite polarity is supplied to electrodes on the opposed laws through conductors connected to an RF generator. In FIGS. 23, and 33-34, each of the first and second jaws 56, 58 include corresponding channels 70, 72, respectively, which are located at a jaw distal end 72, 76 of the first and second jaws 56, 58. FIGS. 33, 34 illustrate that the first and second channels 70, 72 form a bore throughout the thickness of the first and second jaws 56, 58, although it is also contemplated that the first and second channels could be in the form of recesses along the exterior surface of the jaw distal end. Other shapes and orientations of the channels are contemplated and will be apparent to those skilled in the art.

Turning to the ablation instrument 54 of FIGS. 29-34, the first and second jaws 58, 56 are moveable between a spaced apart open position and a closed position. The jaws 58, 56 of the ablation instrument 54 are biased so that they are normally in a closed position, the jaws being moved to an open position by moving the two handle members 60 and 62 towards each other. This action serves to withdraw a push rod 78, as illustrated in FIGS. 30-32, which is pivotally connected to the handle members 60, 62 by links 80, 82. With reference to FIGS. 31 and 32 the distal end of push rod 78 includes two pins 84, 86 which are captured in slots 88, 90 in their respective jaw members 56, 58. When the pins 84, 86 are located in the distal end of the slots 88, 90, the jaws are in the closed position. The jaws 56, 58 open as the pins 84, 86 move proximally in the slots 88, 90 through the withdrawal of the push rod 78 by the closing of the handle members 60, 62.

The jaws 56, 58 also include a spring to bias the jaws toward the closed position. With reference again to FIGS. 31 and 32, the jaws 56, 58 are pivotally connected to each other by means of a pin 92. The pin 92 is secured to the jaw member 58, but is received in an elongated slot 96 in the jaw member 56. The pin 92 is biased to the top of the slot 96, thus biasing the jaws 56, 58 to the closed position by means of leaf spring 98 having one end secured by the pin 94 and the other end captured between two studs 100, 102 carried on the jaw member 56.

With reference to FIGS. 22-27, each of the first and second jaws 56, 58 of the ablation instrument 54 is cooperatively engaged with a separate one of the ends 18, 20 of the guide facility 14. Specifically as shown in FIG. 23, the first end 18 of the guide facility 14 is slidably received within the first channel 70 of the first jaw 56 and the second end 20 is slidably received within second channel 72 of the second jaw 58. Slidable engagement between the ends 18, 20 of the guide facility 14 and the channels 70, 72 of the jaws 56, 58 is accomplished by way of example when the first end 18 of the guide facility 14 is inserted into the channel 70 from an inner edge 104 of the jaw 56, although other engagements are possible without departing from the scope of the invention. Insertion of the first end 18 of the guide facility continues throughout the length of the channel 70 until the first end 18 extends from an outer edge 106 of the first jaw 56. Similarly the second end 20 of the guide facility 14 is inserted into the channel 72 at an inner edge of the second jaw 58 until it extends from the channel along an outer edge of the jaw 58. This defines a cooperative engagement between each of the jaws 56, 58 of the ablation instrument 54 with a separate one of the ends 18, 20 of the guide facility 14. The intermediate portion 22 extends between the first and second ends 18, 20 of the guide facility 14 between the jaws 56, 58 such that both the jaws 56, 58 of the ablation instrument 54 and the guide facility 14 define an area or a loop within which the selected cardiac location is disposed therein. Tension can be provided at either or both of the first and second ends 18, 20 of the guide facility 14 to slidably advance the guide facility 14 through the channels 70, 72 to increase or decrease the area defined by the loop. FIG. 22 illustrates that cooperative engagement between each of the jaws 56, 58 of the ablation instrument 54 with the first and second ends 18, 20 of the guide facility 14 is performed outside of the instrument receiving passage 12 and prior to insertion of the ablation instrument 54 through the instrument receiving channel 12.

As shown in FIG. 24, once engagement between the jaws 56, 58 and the ablation instrument 54 and the first and second ends 18, 20 of the guide facility 14 has been completed, the ablation instrument 54 is inserted through the instrument receiving passage 12. The ablation instrument 54 proceeds along the path that which was previously dissected by the locating instrument 24 and is guided to the selected cardiac location with the aid of the guide facility 14. Tension can be provided at either or both of the ends 18, 20 of the guide facility 14 in the direction of the arrows to decrease the area defined by the loop.

As shown in FIGS. 24-27 the ablation instrument 54 is inserted into the patient's chest and advanced to the left LA adjacent the left pulmonary veins LPV. FIG. 24 illustrates when the ablation instrument 54 is initially inserted into the instrument receiving passage 12. During insertion of the ablation instrument 54, the first and second jaws 56, 58 may be in a substantially closed position until the jaws are advanced to the selected cardiac location, where as illustrated in FIGS. 25 and 26, the jaws 56, 58 are moved to an open position so as to receive the left pulmonary veins between the jaws 56, 58.

With reference to FIGS. 25-26, the opened jaws 56, 58 are advanced around the left atrium LA adjacent the left pulmonary veins LPV with tension being provided at the ends 18, 20 of the guide facility 14 until the jaw distal ends 74, 76 are located forwardly of the selected cardiac location. Due to the slidable engagement between the guide facility 14 and the jaws 56, 58, positioning of the ablation instrument 54 at the left atrium LA is aided by the guide facility 14. The jaw distal ends 74, 76 are advanced towards the selected cardiac location so that the ablating elements 64, 66 engage the cardiac tissue which requires ablation. FIGS. 26-27 show the jaws 56, 58 and the guide facility 14, defining a substantially closed loop around the selected left atrial site such that the site is fully disposed between the ablating elements 64, 66. Tension provided at the ends 18, 20 of the guide facility may assist in positioning the selected cardiac location between the jaws 56, 58 as well as in capturing the cardiac location so that it is in contact with the ablating elements 66, 68. Once the cardiac tissue is captured between the jaws as shown in FIG. 26, the handle members 60, 62 are actuated to move the jaws 56, 58 towards each other thereby clamping the selected cardiac location between the jaws, as best seen in FIG. 27. In this position, the ablation source 68 as shown in FIG. 24 may be activated so as to provide ablation energy to the ablation elements 64, 66.

The ablation source 68 may be an energy generator, a laser source, an electrical voltage, or a cryogenic fluid source, or any other like sources. Activation of the ablation source 68 allows ablation of the selected cardiac location so as to create an ablation line for treating atrial fibrillation. Once the step of ablating has been completed, the jaws 56, 58 of the ablation instrument 54 are moved to an open position so as to release the selected the cardiac location. The ablation instrument 54 is then withdrawn from within the instrument receiving passage 12 while the guide facility 14 is unthreaded from the channel 70, 72 of the jaws 56, 58.

FIG. 28 illustrates ablation of the left atrium LA in accordance with the claimed invention with a second embodiment of an ablation instrument 112, which may similarly be utilized for both open chest and minimally invasive procedures in accordance with the present invention.

Figure 35:
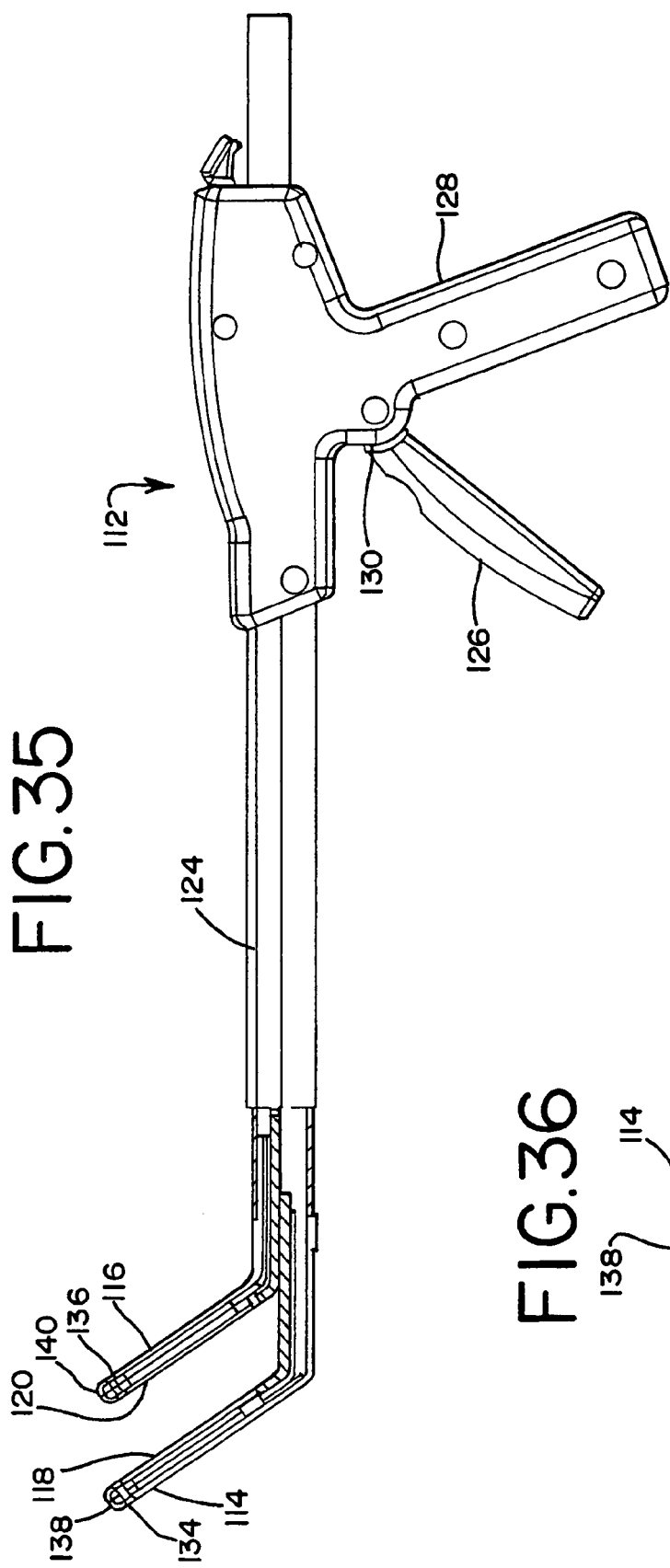
FIG. 35 is a side view of the second embodiment of the ablation instrument with portions shown in section.
Figure 36:
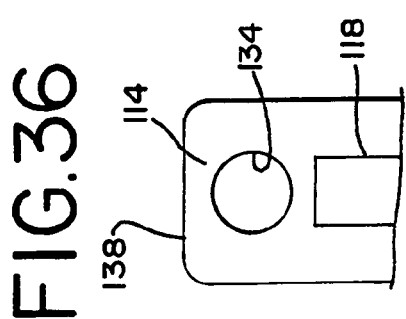
FIG. 36 is an enlarged partial view of the inner edge of one of the jaw assemblies of the ablation instrument in FIG. 35.

Turning to FIGS. 35 and 36, the ablation instrument 112 includes opposed parallel jaw assemblies 114, 116 with jaw assembly 114 being fixed and jaw assembly 116 being movable between an open position as shown in FIG. 35 to a closed position, the spacing between the jaws being substantially uniform or constant. The jaw assemblies 114, 116 may be curved or flat. The fixed jaw assembly 114 includes a fixed ablation element 118 on the inside of the fixed jaw assembly 114 (the "inside" being defined as the side that contacts the tissue to be ablated). Correspondingly, the moveable jaw assembly 116 includes an ablation element 120 which is located on the inside of the jaw assembly 116, as this side is the side that contacts the tissue to be ablated and is in opposing relation to the ablation element 118.

Both ablation elements 118, 120 are likewise connected to an ablation source, generally at 122, which is activated to ablate cardiac tissue when the selected cardiac location is clamped between the jaw assemblies 114, 116. The connection between the ablation elements 118, 120 to the ablation source 122 may be effectuated by a wire or the like which extends through a drive shaft 124 of the ablation instrument 112. Clamping of the selected cardiac location between the jaw assemblies 114, 116 occurs upon actuation of a moveable handle 126. The moveable handle 126 is pivotally moveable in relation to a fixed handle 128 at a handle end 130 so that when the moveable handle 126 is moved toward the fixed handle 128, the jaw assemblies 114, 116 are moved to a closed position to clamp the selected cardiac location for ablation.

FIGS. 35-36 illustrate that each jaw assembly 114, 116 includes channels 134, 136 disposed in jaw distal ends 138, 140 of the jaw assemblies 114, 116 for slidably engaging the guide facility 14. As previously described, a separate one of the ends 18, 20 of the guide facility 14 is inserted into each channel 134, 136 prior to insertion of the ablation instrument through the instrument receiving passage 12. Accordingly, the ablation instrument 112 may be used to carry out the steps of ablating cardiac tissue at the selected cardiac location with the aid of the guide facility 14, similar to the ablation instrument in FIGS. 22-27. FIG. 28 shows cardiac tissue at the left atrium LA being disposed between the jaw assemblies 114, 116 for ablation.

In accordance with another aspect of the invention FIGS. 37-40 illustrate a third embodiment of an ablation instrument, generally at 152. By way of example, the ablation instrument 152 is shown of the type described in FIGS. 35-36 although it also may be of the type described in FIGS. 29-32 as well as any other type of ablation instrument. The ablation instrument 152 includes first and second jaw assemblies 154, 156. Each jaw assembly 154, 156 includes a sensor 158, 160, which is disposed in distal jaw ends or portions 162, 164, and an ablating element 166, 168.

Figure 38:
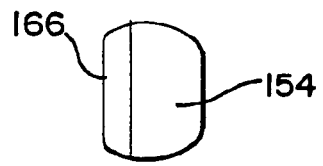
FIG. 38 is a sectional view of the jaw assembly taken along line 38-38 of FIG. 37.

As shown in FIGS. 38-39, the sensors 158, 160 are disposed on the inside of the jaw assemblies 154, 156, as this is the side which contacts the cardiac tissue for ablation. The sensors 158, 160 are preferably disposed distally in relation to the ablating elements 166, 168 and are adapted for sensing the presence of cardiac tissue between the distal jaw ends 162, 164. Upon activation of the sensors 158, 160, a conductive pathway disposed between the sensors at the distal jaw ends 162, 164 senses if cardiac tissue extends forwardly of the ablating elements 166, 168 or, alternatively, the distal jaw ends 162, 164 so as to insure that the selected cardiac location is captured between the jaw assemblies 154, 156 for ablation by the ablating elements 166, 168, as shown in FIG. 39.

In FIG. 40 actuation of the sensors 158, 160 is provided by an energy source 170 which is connected to the ablation instrument 152 by a wire 172 or other like conductive paths. prior to ablation. Prior to ablation, the sensors 158, 160 are activated to determine whether or not an electrical impulse from cardiac tissue is occurring along a conductive pathway disposed between the sensors at the distal jaw ends 162, 164. If the sensors 158, 160 detect the presence of cardiac tissue, the ablation instrument 152 may be repositioned until cardiac tissue is no longer detected between the distal ends 162, 164, as shown by way of example in FIG. 39, and then the ablation elements 166, 168 may be activated to ablate the selected cardiac location.

FIG. 41 illustrates a further aspect of the present invention. An ablation instrument 174 has first and second jaw assemblies 176, 178. Each jaw assembly 176, 178 is moveable between an open position and a closed position, and includes an ablating element 180, 182, a channel 184, 186, and a sensor 188, 190. In accordance with a previously described aspect of the present invention, distal jaw portions 192, 194 of the jaw assemblies 176, 178 may be cooperatively engaged with the first and second ends 18, 20 of the guide facility 14 prior to insertion of the ablation instrument through the instrument receiving passage 12. Accordingly, the ablation instrument 174 may be advanced to the selected cardiac location at the left atrium LA with the aid of the guide facility 14 until the selected cardiac location is disposed between the jaw assemblies 176, 178. Prior to ablation of the cardiac tissue at the selected location, the sensors 188, 190 may be activated to determine the presence of cardiac tissue therebetween. If the sensors 188, 190 do not detect the presence of cardiac tissue then selected cardiac location is ablated. Other variations in ablation instrument 174 are also possible. For example, although the sensors 188, 190 are shown as distally located in relation to the channels 184, 186 on each distal jaw portion 192, 194, it is also possible that the sensors 188, 190 could be position proximally in relation to the channels 184, 186.

FIGS. 42-44 illustrates a modified method and apparatus for ablating a selected cardiac location which employs multiple guide facilities in a different orientation relative to the selected cardiac location than described above. In FIGS. 42-44 first and second guide facilities 14A and 14B are similar to the previously described guide facility 14, and like parts will be shown and described with the same numbers following by corresponding letters A or B, as appropriate.

In FIG. 42, the first guide facility, generally indicated at 14A, is inserted into the incision which defines an opening 196 into the patient's chest and instrument receiving passage. The guide facility 14A is advanced to the selected cardiac location, such as for example the atrial tissue adjacent a pair of pulmonary veins. The locating instrument 24 may be, and preferably is, used to facilitate introduction of the first guide facility 14A. In FIG. 42, the locating instrument has a handle member 200 at its proximal end and includes a control knob 202 which is operatively connected to the distal end by a suitable actuating linkage so that movement of the control knob causes corresponding movement of the distal end in a desired direction. As previously described, the locating instrument may be repositioned to dissect cardiac tissue and debris at the selected location above, below and around the selected location and it further may utilize any of the instruments previously described as being insertable into one of the passageways 32 (FIGS. 10-11) of the locating instrument such as for example, the endoscope 34 to permit visualization of the selected location.

FIG. 42 shows the first end 18A of the guide facility 14A at a location which is forward ("forward" being defined as the direction that the distal end of the instrument is pointing). The first guide facility 14A is capable of being advanced beyond the distal end of the locating instrument and may be disengaged from the locating instrument, when it is desired to withdraw the locating instrument. The first end 18A of the guide facility is preferably advanced along one side of the selected location in the vicinity of the selected cardiac location and, in particular, is preferably placed adjacent the selected location where one of the jaws of the ablation instrument will be placed. In FIG. 42, the first guide facility is advanced in a forward direction below the pair of pulmonary veins in the vicinity of the atrial tissue which is selected for ablation.

In FIG. 42 a second incision or opening 204 is made which is preferably, but not exclusively, located between the ribs, and other locations are possible as previously discussed above. The second incision 204 permits extension of the guide facility to a location outside of the patient. The grasper 36 may be inserted through the second incision and advanced to the selected location until its grasping portion 52 clamps the first end 18A of the first guide facility 14A to facilitate extraction of the first guide facility. Introduction of the grasper through the second opening to the selected location may be aided by a suitable locating instrument which may be similar to the locating instrument 24 described above. It is possible to use the same locating instrument as that used to position the first guide facility, and if used, the first guide facility 14A is preferably disengaged and positioned adjacent the selected location prior to withdrawal and repositioning of the locating instrument. Other instruments may also be used to aid introduction and positioning of the grasper and these instruments may be inserted through the second opening 204 or through a separate incision such as that shown in FIG. 42 for the endoscope 34.

In FIG. 43, the grasper 36 is retracted or withdrawn through the second incision 204 and, in doing so, also draws the first end 18A of the guide facility through the incision 204. As shown in FIG. 43, the first end 18A extends to a position outside of the patient. Likewise, the second end 20A of the guide facility 14A extends to a position outside the opening defined by the first incision 196. Thus, the guide facility extends throughout the entire instrument receiving passage defined between the two incision openings 196, 204 with the intermediate portion 22A of the guide facility engaging the selected location.

The steps are preferably repeated for the second guide facility 14B so that its first and second ends 18B, 20B extends outside the respective openings of the patient and the intermediate portion 22B engages the selected cardiac location. As compared to the first guide facility 14A, the second guide facility 14B is preferably, but not exclusively, positioned at a different side of the selected location and even more preferably at a location where it is desired to place the other jaw of the ablation instrument. In FIG. 44, the second guide facility 14B is shown following a path above the pair of pulmonary veins and in the vicinity of the atrial tissue. In this regard, the first and second guide facilities are disposed at different, and generally opposite, sides of the pair of pulmonary vein to facilitate access to the atrial tissue on opposite sides selected ablation site. Introduction of the second guide facility 14B also may employ one or both of the locating instrument 24 and grasper 36. The locating instrument 24 may be disengaged from the first guide facility 14A and withdrawn from the instrument receiving passage to allow the second guide facility to be inserted into one of the passageways 32, or, alternatively, the locating instrument may be left within the instrument receiving passage and the second guide facility may be advanced to the selected location through one of the passageways 32.

It is contemplated that the method may be utilized by employing the first guide facility. In this regard, the method may be employed without the introduction of the second guide facility, if desired. The first guide facility may be introduced, as previously described, into the first opening of the instrument receiving passage and advanced to the selected cardiac location. By way of example, and not limitation, the first guide facility may be advanced to posterior surface of the atrium below the pulmonary veins. The forward advancing end of the guide facility is further advanced past the selected cardiac location and is positioned outside of the second opening of the instrument receiving passage. Then at least one jaw of the ablation instrument engages one end of the first guide facility as the ablation instrument is guided to the selected cardiac location.

The method of FIGS. 42-44 may employ any of the previously described ablation instruments such as those shown and described in FIGS. 29-34 or FIGS. 35-36 and any other modifications thereof. FIG. 44 shows each jaw 206A, 206B of the ablation instrument engaging a separate second end 22A and 22B of the guide facilities. The channel defined in each jaw receives a separate end which is inserted therein. In accordance with previously described embodiments each jaw may be in slidable engagement with the end of the respective guide facility and tension is provided to the inserted end of the respective guide facility to advance the jaws in a forward direction toward the selected location. It is contemplated that other engagements are also possible. For example, one end or portion of the guide facility may be attached to the jaw, or another portion of the ablation instrument, by tying, clamping, hooking, looping or the like to provide tension to the attached ends of the guide facility and thus free the operators hands for other portions of the procedure.

FIG. 44 shows the second ends 20A, 20B of each guide facility attached to the respective jaw 206A, 206B to provide tension force. Tensioning force may also be applied to the first ends 18A and 18B to advance the ablation instrument to the selected location. For example in FIG. 44, pulling the first ends 18A, 18B of the guide facilities may be used to advance the jaws of the ablation instrument around the pair of pulmonary veins in the vicinity of the atrial tissue adjacent the veins.

Other variations in the method of the present invention are also possible. For example, the method may be performed on the epicardial surface of the heart where the method includes the step of separating the pericardium from the selected cardiac location prior to ablation by the ablation instrument. The jaws of the ablation instrument are inserted through an incision made in the pericardium P and advanced into the pericardial space.

In addition, ablation of the selected cardiac location may be performed by any of the ablation instruments described as well as other ablation instruments known to those skilled in the art. The present invention may be utilized to create a plurality of ablation lines at selected cardiac locations at different areas of the hearts for treating atrial fibrillation. These ablation lines may be disposed to create an electrical maze in the atria such as that utilized in the Maze procedure. Although the present invention is shown as ablating the left atrium LA adjacent the left pulmonary veins LPV, is realized that the method of ablation may be performed on other areas of the heart. These areas include but are not limited to the atrium adjacent the right pulmonary veins, the left atrial appendage, the right atrial appendage, and other heart locations.

Another advantage of the ablation instrument is that it can easily be adapted to a minimally invasive approaches such as intercostal, sub-xyphoid or other similar approaches. The ablation instrument may been reduced to a 5 mm diameter device, and can probably be reduced to 3 mm or less.

Accordingly, an apparatus and method for performing transmural ablation has been provided that meets all the objects of the present invention. While the invention has been described in terms of certain preferred embodiments, there is no intent to limit the invention to the same. Instead it is to be defined by the scope of the appended claims.

What is claimed is:

1. A method for ablating the pulmonary veins of a patient including:
    making at least one percutaneous incision to define at least one opening of an instrument receiving passage;
    providing at least one flexible elongated guide facility having a first end, a second end and an intermediate portion extending between the first and second ends;
    providing an ablation instrument including at least a pair of relatively movable clamping jaws adapted to be connected to an ablation activation source, the jaws being disposed to engage cardiac tissue at a selected cardiac location to ablate tissue therebetween;
    introducing the first end of the at least one guide facility through selected one of the at least one opening of the instrument receiving passage to a selected cardiac location adjacent one of the right and left pulmonary veins;
    advancing the guide facility to the selected cardiac location such that the intermediate portion engages the selected cardiac location;
    extending the first end of the at least one guide facility through selected one of the at least one opening of the instrument receiving passage to a position disposed outside the instrument receiving passage such that the first and second ends are positioned outside of the instrument receiving passage and the intermediate portion engages the selected cardiac location;
    engaging one jaw of the ablation instrument with one of the ends of the guide facility;
    inserting the ablation instrument through the instrument receiving passage;
    guiding the ablation instrument to the selected cardiac location with the aid of the guide facility such that the cardiac tissue at the selected location is disposed between the jaws; and
    ablating the cardiac tissue at the selected location.

2. The method of claim 1 wherein making at least one percutaneous incision includes making a percutaneous incision.

3. The method of claim 1 wherein advancing includes pulling the first end of the at least one guide facility around the cardiac tissue at the selected cardiac location such that the guide facility is circumferentially positioned in relation to the cardiac tissue.

4. The method of claim 1 wherein engaging at least one jaw includes positioning at least one jaw of the ablation instrument in slidable engagement with one of the ends of the at least one guide facility while the ablation instrument is outside of the instrument receiving passage.

5. The method of claim 1 wherein engaging at least one jaw includes attaching at least one of the jaws of the ablation instrument with one of the ends of the guide facility.

6. The method of claim 1 wherein guiding the ablation instrument includes providing tension to one or both ends of the guide facility so that the ablation instrument advances to the selected location.

7. A method for ablating the pulmonary veins of a patient including:
   making a percutaneous incision to define an instrument receiving passage;
   providing a flexible elongated guide facility having a first end, a second end and an intermediate portion extending between the first and second ends;
   providing an ablation instrument including at least a pair of relatively movable clamping jaws adapted to be connected to an ablation activation source, the jaws being disposed to engage cardiac tissue at a selected cardiac location to ablate tissue therebetween;
   introducing the first end of the guide facility through the instrument receiving passage to a selected cardiac location adjacent one of the right and left pulmonary veins;
   advancing the guide facility to the selected cardiac location such that the intermediate portion engages the selected cardiac location;
   extending the first end of the guide facility to a position disposed outside the instrument receiving passage such that the first and second ends are positioned outside of the instrument receiving passage and the intermediate portion engages the selected cardiac location;
   cooperatively engaging each of the jaws of the ablation instrument with a separate one of the ends of the guide facility;
   inserting the ablation instrument through the instrument receiving passage;
   guiding the ablation instrument to the selected cardiac location with the aid of the guide facility such that the cardiac tissue at the selected location is disposed between the jaws; and
   ablating the cardiac tissue at the selected location.

8. The method of claim 7 wherein the step of advancing includes pulling the first end of the guide facility around the cardiac tissue at the selected cardiac location such that the guide facility is circumferentially positioned in relation to the cardiac tissue.

9. An apparatus for ablating cardiac tissue of a patient comprising:
   an elongated body including a distal end and a proximal end;
   first and second jaws carried at the distal end and movable between a spaced-apart open position and a closed position, each jaw comprising an ablating element connected to an ablation activation source for ablating cardiac tissue located between the jaws, each jaw defining a channel which is distally located in relation to the ablating element; and
   a flexible elongated guide facility having first and second ends and an intermediate portion extending between the first and second ends, upon positioning of the intermediate portion around a selected cardiac location of the patient each end of the guide facility is slidably received within a separate channel of the jaws so as to guide the jaws to the selected cardiac location for ablation thereof.

10. The apparatus of claim 9 wherein the jaws and the guide facility define a substantially closed loop around the selected cardiac location, tension being provided at one or both of the first and second ends of the guide facility to decrease the area defined by the loop and capture the selected cardiac location between the jaws.

11. An apparatus for epicardially ablating cardiac tissue of a patient comprising:
   an elongated body including a distal end and a proximal end;
   first and second jaws carried at the distal end and movable between a spaced-apart open position and a closed position, each jaw carrying a separate conductive element and each conductive element being adapted for connection to an opposite pole of a bipolar RF energy an activation source for ablating cardiac tissue located between the jaws at a selected location of the heart;
   at least one flexible elongated guide facility having first and second ends and an intermediate portion extending between the first and second ends and adapted to be placed around an exterior surface of the heart at the selected location; and
   at least one of the jaws being adapted for removable connection to the elongated guide facility and operable to be constrained by such guide facility for advancing the jaws to the exterior surface and locating the jaws at the selected location for ablation.

12. The apparatus of claim 11 wherein each jaw defines a channel which is distally located in relation to the ablating element, and one end of the at least one guide facility is engaged within a selected one channel of one of the jaws.

13. The apparatus of claim 11 wherein each jaw defines a channel which is distally located in relation to the ablating element, each end of the guide facility is slidably received within a separate channel of the jaws.

* * * * *